US012788424B2

(12) United States Patent
Barnes et al.

(10) Patent No.: US 12,788,424 B2

(45) Date of Patent: Nov. 10, 2026

(54) ROTATING AND OSCILLATING SURGICAL BONE REMOVAL TOOL WITH TOOL EXPOSURE MECHANISM AND LOCKING COLLET

(71) Applicant: Medtronic PS Medical, Inc., Goleta, CA (US)

(72) Inventors: Milton F. Barnes, Grand Prairie, TX (US); Haoran Li, Flower Mound, TX (US); Michael Vu, Grand Prairie, TX (US); Mohamed S. Mohammed, Euless, TX (US); Bret R. Hauser, Fort Worth, TX (US); Mahin Maharjan, Arlington, TX (US)

(73) Assignee: Medtronic PS Medical, Inc., Goleta, CA (US)

( * ) Notice: Subject to any disclaimer, the term of this patent is extended or adjusted under 35 U.S.C. 154(b) by 414 days.

(21) Appl. No.: 18/511,124

(22) Filed: Nov. 16, 2023

(65) Prior Publication Data

US 2024/0156482 A1 May 16, 2024

Related U.S. Application Data

(60) Provisional application No. 63/442,222, filed on Jan. 31, 2023, provisional application No. 63/425,872, (Continued)

(51) Int. Cl.

*A61B 17/32* (2006.01)

*A61B 17/3207* (2006.01)

(52) U.S. Cl.

CPC .................. *A61B 17/32002* (2013.01); *A61B 17/320758* (2013.01); *A61B 2017/320008* (2013.01)

(58) Field of Classification Search

CPC ...... A61B 17/32002; A61B 17/320758; A61B 17/1622; A61B 17/1624

See application file for complete search history.

(56) References Cited

U.S. PATENT DOCUMENTS

| | | | |
|---|---|---|---|
| 233,709 | A | 10/1880 | Starr |
| 288,676 | A | 11/1883 | Stearns |

(Continued)

FOREIGN PATENT DOCUMENTS

| | | | |
|---|---|---|---|
| CH | 686113 | A5 | 1/1996 |
| CN | 1150073 | A | 5/1997 |

(Continued)

OTHER PUBLICATIONS

International Search Report PCT/US2023/080139 dated Apr. 23, 2024, 19pp.

(Continued)

*Primary Examiner* — Erin McGrath

(74) *Attorney, Agent, or Firm* — Carter, DeLuca & Farrell, LLP

(57) ABSTRACT

A surgical device for cutting or shaving bone or tissue includes an outer housing having a collet secured to an inner peripheral surface thereof including one or more apertures defined therein. A housing includes an elongated tube extending therefrom configured to support a surgical tool at a distal end thereof. A gear assembly is disposed within the housing and is configured to drive the surgical tool, the gear assembly includes a drive gear housing selectively moveable within the housing to switch the gear assembly between an oscillation mode and a rotation mode for driving the surgical tool. A motor is operably coupled to the gear assembly, such that, upon activation thereof, the motor oscillates or rotates the surgical tool depending upon the position of the drive gear housing within the housing.

20 Claims, 37 Drawing Sheets

Related U.S. Application Data filed on Nov. 16, 2022, provisional application No. 63/425,870, filed on Nov. 16, 2022.

(56) References Cited

U.S. PATENT DOCUMENTS 1,043,098 A 11/1912 Gross
1,053,709 A 2/1913 Collins
1,112,349 A 9/1914 Barnes
1,209,362 A 12/1916 Turner
1,539,439 A 5/1925 Smith
1,862,337 A 6/1932 Emrick
2,477,058 A 7/1949 Harborne et al.
2,512,033 A 6/1950 Metz
2,522,388 A 9/1950 Madsen
2,596,594 A 5/1952 Petre
2,682,184 A 6/1954 Szarkowski
2,726,872 A 12/1955 Onsrud
2,766,791 A 10/1956 Givens
2,773,693 A 12/1956 Chittenden
3,043,634 A 7/1962 Coley
3,136,347 A 6/1964 Linquist
3,589,826 A 6/1971 Fenn
3,637,225 A 1/1972 Schmuck
3,835,858 A 9/1974 Hagen
3,943,986 A 3/1976 Lejdegard
4,035,100 A 7/1977 Kruger et al.
4,047,722 A 9/1977 Nielsen et al.
4,078,593 A 3/1978 Benitz
4,107,949 A 8/1978 Wanner et al.
4,123,074 A 10/1978 Wanner
4,146,240 A 3/1979 Nielsen
4,185,383 A 1/1980 Heimke et al.
4,378,053 A 3/1983 Simpson
4,502,734 A 3/1985 Allan
4,512,692 A 4/1985 Nielsen
4,565,472 A 1/1986 Brennsteiner et al.
4,594,036 A 6/1986 Hogenhout
4,655,651 A 4/1987 Hunger et al.
4,823,468 A 4/1989 Kollegger
4,830,000 A 5/1989 Shutt
4,917,274 A 4/1990 Asa et al.
5,009,440 A 4/1991 Manschitz
5,116,353 A 5/1992 Green
5,203,654 A 4/1993 Henderson
5,256,147 A 10/1993 Vidal et al.
5,263,786 A 11/1993 Kageyama
5,286,145 A 2/1994 Kleine
5,352,234 A 10/1994 Scott
5,382,249 A 1/1995 Fletcher
5,421,682 A 6/1995 Obermeier et al.
5,439,005 A 8/1995 Vaughn
5,466,101 A 11/1995 Meyen
5,487,626 A 1/1996 Von Holst et al.
5,499,985 A 3/1996 Hein et al.
5,505,737 A 4/1996 Gosselin et al.
5,549,634 A 8/1996 Scott et al.
5,569,256 A 10/1996 Vaughn et al.
D377,982 S 2/1997 Walen
5,601,560 A 2/1997 Del Rio et al.
5,634,933 A 6/1997 McCombs et al.
5,697,158 A 12/1997 Klinzing et al.
5,720,749 A 2/1998 Rupp
5,735,535 A 4/1998 McCombs et al.
5,741,263 A 4/1998 Umber et al.
5,782,836 A 7/1998 Umber et al.
5,807,040 A 9/1998 Bongers-Ambrosius et al.
5,810,802 A 9/1998 Panescu et al.
5,833,704 A 11/1998 McCombs et al.
5,851,094 A 12/1998 Strand et al.
5,888,200 A 3/1999 Walen
5,893,851 A 4/1999 Umber et al.
5,928,241 A 7/1999 Menut et al.
5,941,891 A 8/1999 Walen
5,964,555 A 10/1999 Strand
5,989,257 A 11/1999 Tidwell et al.
6,000,940 A 12/1999 Buss et al.
6,007,541 A 12/1999 Scott
6,033,408 A 3/2000 Gage et al.
6,062,575 A 5/2000 Mickel et al.
6,209,886 B1 4/2001 Estes et al.
6,261,035 B1 7/2001 Moores, Jr. et al.
6,267,763 B1 7/2001 Castro
RE37,358 E 9/2001 Del Rio et al.
6,290,525 B1 9/2001 Jacobi
6,409,221 B1 6/2002 Robinson et al.
6,447,484 B1 9/2002 Briscoe et al.
6,607,533 B2 8/2003 Del Rio et al.
6,612,588 B2 9/2003 Ostermeier et al.
6,688,610 B2 2/2004 Huggins et al.
6,723,101 B2 4/2004 Fletcher et al.
6,733,218 B2 5/2004 Del Rio et al.
D492,412 S 6/2004 Desoutter et al.
6,746,153 B2 6/2004 Del Rio et al.
6,780,189 B2 8/2004 Tidwell et al.
6,811,190 B1 11/2004 Ray et al.
6,976,815 B2 12/2005 Berglow et al.
7,001,391 B2 2/2006 Estes et al.
7,011,661 B2 3/2006 Riedel et al.
7,066,940 B2 6/2006 Riedel et al.
D536,791 S 2/2007 Eskridge et al.
7,261,169 B2 8/2007 Kleine et al.
7,374,375 B2 5/2008 Kleine et al.
7,429,154 B2 9/2008 Kleine et al.
7,465,309 B2 12/2008 Walen
7,488,327 B2 2/2009 Rathbun et al.
7,497,860 B2 3/2009 Carusillo et al.
7,549,992 B2 6/2009 Shores et al.
7,559,927 B2 7/2009 Shores et al.
D609,810 S 2/2010 Cote et al.
7,669,308 B2 3/2010 Oshnock et al.
7,691,106 B2 4/2010 Schenberger et al.
7,722,054 B2 5/2010 Young
D617,900 S 6/2010 Kingsley et al.
D617,901 S 6/2010 Unger et al.
D617,902 S 6/2010 Twomey et al.
D617,903 S 6/2010 Unger et al.
7,766,585 B2 8/2010 Vasudeva et al.
D631,962 S 2/2011 Dorman
D636,082 S 4/2011 Cote et al.
7,922,720 B2 4/2011 May et al.
D641,468 S 7/2011 Ruiz, Sr. et al.
8,043,292 B2 10/2011 Carusillo
D648,021 S 11/2011 Dorman
D666,294 S 8/2012 Miles et al.
8,361,068 B2 1/2013 McClurken
8,419,760 B2 4/2013 Wiebe, III
8,518,065 B2 8/2013 Shores
D692,134 S 10/2013 Lee-Sepsick
8,597,316 B2 12/2013 McCombs
8,702,710 B2 4/2014 Carusillo
8,801,713 B2 8/2014 del Rio et al.
8,893,820 B2 11/2014 Barhitte et al.
D728,098 S 4/2015 Schad et al.
D728,099 S 4/2015 Schad et al.
D744,650 S 12/2015 Catron et al.
D746,457 S 12/2015 Swick et al.
D747,477 S 1/2016 Freigang et al.
D753,826 S 4/2016 Eggeling et al.
9,333,561 B2 5/2016 Nakai et al.
9,597,737 B2 3/2017 Hecht
10,080,579 B2 9/2018 Cihak et al.
10,314,610 B2 6/2019 Dexter et al.
10,588,640 B2 3/2020 Steinhauser et al.
11,154,319 B2 10/2021 Dexter et al.
2002/0105149 A1 8/2002 Karst
2002/0151902 A1 10/2002 Riedel et al.
2002/0171208 A1 11/2002 Lechot et al.
2003/0060841 A1 3/2003 Del Rio et al.
2003/0097133 A1 5/2003 Green et al.
2003/0130663 A1 7/2003 Walen
2003/0140743 A1 7/2003 Ofentavsek
2003/0163134 A1 8/2003 Riedel et al.
2003/0229351 A1 12/2003 Tidwell et al.
2005/0027282 A1 2/2005 Schweikert et al.

(56) References Cited

U.S. PATENT DOCUMENTS

| | | | |
|---|---|---|---|
| 2005/0072007 | A1 | 4/2005 | Proulx |
| 2005/0232715 | A1 | 10/2005 | Baumann et al. |
| 2006/0053974 | A1 | 3/2006 | Blust |
| 2007/0172321 | A1 | 7/2007 | Nagai |
| 2007/0282329 | A1 | 12/2007 | Kawano |
| 2008/0033280 | A1 | 2/2008 | Lubock et al. |
| 2009/0024129 | A1 | 1/2009 | Gordon et al. |
| 2009/0312779 | A1 | 12/2009 | Boykin et al. |
| 2010/0063524 | A1 | 3/2010 | McCombs |
| 2010/0076477 | A1 | 3/2010 | Jezierski et al. |
| 2011/0022069 | A1 | 1/2011 | Mitusina |
| 2011/0190803 | A1 | 8/2011 | To et al. |
| 2011/0218562 | A1 | 9/2011 | Viola et al. |
| 2011/0238070 | A1 | 9/2011 | Santangelo et al. |
| 2011/0270293 | A1 | 11/2011 | Malla et al. |
| 2011/0270294 | A1 | 11/2011 | Rubin |
| 2012/0070220 | A1 | 3/2012 | Ruiz, Sr. et al. |
| 2012/0259336 | A1 | 10/2012 | del Rio et al. |
| 2012/0259337 | A1 | 10/2012 | del Rio |
| 2013/0110147 | A1 | 5/2013 | Dame |
| 2013/0116659 | A1 | 5/2013 | Porter |
| 2013/0138096 | A1 | 5/2013 | Benn |
| 2013/0144267 | A1 | 6/2013 | Chan et al. |
| 2013/0245704 | A1 | 9/2013 | Koltz et al. |
| 2013/0296848 | A1 | 11/2013 | Allen, IV et al. |
| 2013/0304069 | A1 | 11/2013 | Bono et al. |
| 2014/0056656 | A1 | 2/2014 | Bae et al. |
| 2014/0124231 | A1 | 5/2014 | Hessenberger et al. |
| 2014/0163558 | A1 | 6/2014 | Cosgrove et al. |
| 2014/0262408 | A1 | 9/2014 | Woodard |
| 2014/0303624 | A1 | 10/2014 | del Rio et al. |
| 2014/0336654 | A1 | 11/2014 | Pilgeram |
| 2014/0343454 | A1 | 11/2014 | Miller et al. |
| 2014/0350561 | A1 | 11/2014 | Dacosta et al. |
| 2014/0371752 | A1 | 12/2014 | Anderson |
| 2016/0278802 | A1 | 9/2016 | Cihak et al. |
| 2018/0140308 | A1 | 5/2018 | Anderson |
| 2018/0185052 | A1 | 7/2018 | Zhou et al. |
| 2019/0388115 | A1 | 12/2019 | Nguyen |
| 2022/0338895 | A1 | 10/2022 | Bono et al. |

FOREIGN PATENT DOCUMENTS

| | | | |
|---|---|---|---|
| CN | 103447599 | A | 12/2013 |
| CN | 103458805 | A | 12/2013 |
| DE | 88152618 | | 3/1989 |
| DE | 102012101259 | A1 | 8/2013 |
| EP | 0293327 | A2 | 11/1988 |
| EP | 0216354 | B1 | 7/1991 |
| EP | 1101459 | B1 | 2/2006 |
| EP | 1289714 | B1 | 8/2008 |
| EP | 1514034 | B1 | 10/2011 |
| GB | 2129730 | A | 5/1984 |
| JP | 2014516611 | A | 7/2014 |
| RU | 2077275 | C1 | 4/1997 |
| WO | 9608343 | A1 | 3/1996 |
| WO | 0166024 | A1 | 9/2001 |
| WO | 0189769 | A1 | 11/2001 |
| WO | 2012138337 | A1 | 10/2012 |
| WO | 2014037134 | A1 | 3/2014 |
| WO | 2014176060 | A1 | 10/2014 |

OTHER PUBLICATIONS

International Search Report and Written Opinion for International Application No. PCT/US2016/018686 dated Jul. 12, 2016 (4 pgs).

International Search Report PCT/US2023/080169, dated Mar. 4, 2024, 12pp.

ROTATING AND OSCILLATING SURGICAL BONE REMOVAL TOOL WITH TOOL EXPOSURE MECHANISM AND LOCKING COLLET

CROSS REFERENCE TO RELATED APPLICATIONS

This application claims the benefit of and priority to U.S. Provisional Patent Application Nos. 63/425,872 and 63/425,870 filed on Nov. 16, 2022 and U.S. Provisional Patent Application No. 63/442,222 filed on Jan. 31, 2023, the entire contents of all of which are hereby incorporated herein by reference.

FIELD

The present disclosure is generally directed to devices and systems for cutting and treating bone and hard tissue and biomaterials. The devices and systems of the present disclosure may be particularly suitable for orthopedical applications and other surgical procedures requiring bone removal.

BACKGROUND

Devices and systems in accordance with the present disclosure may be suitable for a variety of procedures including orthopedical surgical procedures, spinal procedures, cranial procedures, and other procedures requiring bone or hard tissue removal. During a given procedure, a motor is used to power a drill disposed at a distal end of the surgical tool. Typically, the tool is rotated at a very high RPM which allows the drill dissecting tip of the tool to plunge into the bone or, in some instances, cut or shave the bone using one or more flutes on the drill dissecting tip. However, in some instances, the rotating drill tip if improperly handled can catch adjacent tissue, cause adjacent tissue to wrap around the drill tip when a surgeon is trying to steer clear of delicate tissue, nerves, and ligaments and incidental contact with the drill tip.

One solution has been to manufacture surgical bone cutting/dissecting tools that use a drill bit and motor that employs an oscillatory motion to cut bone and hard tissue. By oscillating the drill bit, tissue is less prone to catch and wrap around the drill bit if the drill bit contacts tissue.

SUMMARY

Provided in accordance with the present disclosure is a surgical device for cutting or shaving bone or tissue and includes an outer housing having a collet secured to an inner peripheral surface thereof including a series of apertures defined about a circumference therein. A housing includes an elongated tube that extends therefrom that is configured to support a surgical tool at a distal end thereof. A gear assembly is disposed within the housing and is configured to drive the surgical tool. The gear assembly includes a drive gear housing that is selectively moveable within the housing to switch the gear assembly between an oscillation mode and a rotation mode for driving the surgical tool. A motor is operably coupled to the gear assembly, such that, upon activation thereof, the motor oscillates or rotates the surgical tool depending upon the position of the drive gear housing within the housing.

In aspects according to the present disclosure, the housing includes a slot defined in a proximal end thereof that communicates with a post that extends from the drive gear housing such that upon movement of the housing the slot correspondingly moves the post within the slot. In other aspects according to the present disclosure, the slot is arcuate and the post moves within the slot upon rotation of the housing relative to the collet. In yet other aspects according to the present disclosure, the surgical device further includes a lever lock that operably couples to the housing and wherein, upon actuation, the lever lock allows a user to selective rotate the housing relative to the collet and, upon release, the lever lock allows a user to lock the lever lock in one of the series of apertures defined within the collet.

In aspects according to the present disclosure, when disposed in the oscillation mode the gear assembly operably engages a link that oscillates a swing gear at a rotation angle β, the rotation angle β being dependent on the distance between an axis of the motor and an axis of the swing gear. In other aspects according to the present disclosure, the distance between the axis of the motor and the axis of the swing gear changes upon rotation of the housing relative to the collet thereby changing the rotation angle β.

In aspects according to the present disclosure, a lever lock is included that operably couples to the housing and wherein, upon actuation, the lever lock allows a user to selective rotate the housing relative to the collet and, upon release, the lever lock allows a user to lock the lever lock in one of the series of apertures defined within the collet and wherein each of the series of apertures sets the rotation angle β of the swing gear. In other aspects according to the present disclosure, one or more of the series of apertures defines a rotation angle β of the swing gear of about 59°, about 68° or about 76°.

Provided in accordance with the present disclosure is a surgical device for cutting or shaving bone or tissue and includes an outer housing having a collet secured to an inner peripheral surface thereof including a series of apertures defined about a circumference therein. A housing includes an elongated tube that extends therefrom that is configured to support a surgical tool at a distal end thereof. A gear assembly is disposed within the housing and is configured to drive the surgical tool, the gear assembly includes a drive gear housing selectively moveable within the housing to switch the gear assembly between an oscillation mode and a rotation mode for driving the surgical tool. A motor is operably coupled to the gear assembly, such that, upon activation thereof, the motor oscillates or rotates the surgical tool depending upon the position of the drive gear housing within the housing, wherein when disposed in the rotational mode the gear assembly operably engages a direct drive gear that couples to an idle gear that drives the surgical tool.

In aspects according to the present disclosure, the housing includes a slot defined in a proximal end thereof that communicates with a post that extends from the drive gear housing such that upon movement of the housing the slot correspondingly moves the post within the slot. In other aspects according to the present disclosure, the slot is arcuate and the post moves within the slot upon rotation of the housing relative to the collet.

In aspects according to the present disclosure, a lever lock is included that operably couples to the housing and wherein, upon actuation, the lever lock allows a user to selective rotate the housing relative to the collet and, upon release, the lever lock allows a user to lock the lever lock in one of the series of apertures defined within the collet. In other aspects according to the present disclosure, upon actuation, the lever lock allows a user to selective rotate the housing relative to the collet and, upon release, the lever lock allows a user to lock the lever lock in one of the series of apertures defined within the collet and wherein rotation of the housing to one of the series of apertures, in turn, moves the drive gear housing to configure the surgical device in a rotational mode. In still other aspects according to the present disclosure, upon rotation of the housing relative to the collet, the post moves along the slot to disengage a series of gears associated with the oscillation mode and engage a series of gears associated with the rotational mode. In yet other aspects according to the present disclosure, the drive gear housing includes a pin groove defined therein which is configured to at least partially seat the idle gear therein, the pin groove configured to restrict movement of the drive gear housing in a linear direction as the housing rotates.

Provided in accordance with the present disclosure is a surgical device for cutting or shaving bone or tissue and includes an outer housing having a collet secured to an inner peripheral surface thereof including a series of apertures defined about a circumference therein. A housing includes an elongated tube that extends therefrom that is configured to support a surgical tool at a distal end thereof. A gear assembly is disposed within the housing and is configured to drive the surgical tool, the gear assembly including a drive gear housing selectively moveable within the housing to switch the gear assembly between an oscillation mode and a rotation mode for driving the surgical tool. A motor is operably coupled to the gear assembly, such that, upon activation thereof, the motor oscillates or rotates the surgical tool depending upon the position of the drive gear housing within the housing, wherein when disposed in the rotational mode the gear assembly operably engages a direct drive gear that couples to an idle gear that drives the surgical tool and wherein when disposed in the oscillation mode the gear assembly operably engages a link that oscillates a swing gear at a rotation angle $\beta$, the rotation angle $\beta$ being dependent on the distance between the axis of the motor and the axis of the swing gear.

In aspects according to the present disclosure, the housing includes a slot defined in a proximal end thereof that communicates with a post that extends from the drive housing such that upon movement of the housing the slot correspondingly moves the post within the slot. In other aspects according to the present disclosure, the slot is arcuate and the post moves within the slot upon rotation of the housing relative to the collet. In aspects according to the present disclosure, a lever lock is included that operably couples to the housing and wherein, upon actuation, the lever lock allows a user to selective rotate the housing relative to the collet and, upon release, the lever lock allows a user to lock the lever lock in one of the series of apertures defined within the collet.

In aspects according to the present disclosure, the surgical tool includes a drill bit that is configured to cut or shave tissue when disposed in an oscillating mode or a rotation mode.

Provided in accordance with the present disclosure is a surgical device for cutting or shaving bone or tissue and includes a housing including an elongated tube extending therefrom and configured to receive the shaft of a surgical tool therein. A gear assembly is disposed within the housing and includes a driveshaft configured to drive the surgical tool. A locking collar is disposed at a distal end of the housing and includes a helical groove defined therein configured to at least partially receive a portion of a ball bearing. A collet is disposed within the locking collar and includes a pocket defined therein for retaining an opposing portion of the ball bearing, the collet moveable within the locking collar between a proximal position and a distal position.

A locking bearing is disposed within the collet and is configured to receive a distal end of the driveshaft of the gear assembly, the distal end of the driveshaft configured to operably receive the proximal end of the shaft of the surgical tool upon initial insertion thereof when the collet is disposed in the proximal position. After insertion of the proximal end of the shaft of the surgical tool into the distal end of the driveshaft, the locking collar is rotated in a first direction to move the ball bearing along the helical groove which, in turn, correspondingly moves the ball bearing and the pocket to translate the collet to the distal position and force the locking bearing over the distal end of the driveshaft to securely engage the distal end of the driveshaft to the proximal end of the surgical tool.

In aspects according to the present disclosure, the proximal end of the surgical tool and the distal end of the driveshaft include cooperating mechanically interfacing elements to induce initial engagement thereof.

In aspects according to the present disclosure, the distal end of the driveshaft includes a plurality of fork-like tines that cooperate in a spring-like manner to facilitate engagement with the proximal end of the tool shaft upon insertion thereof. In other aspects according to the present disclosure, upon rotation of the locking collar in the first direction, the locking bearing compresses the plurality of fork-like tines against the proximal end of the tool shaft to secure the tool shaft thereto.

In aspects according to the present disclosure, upon rotation of the locking collar in a second direction, opposite the first direction, the ball bearing moves along the helical groove which, in turn, correspondingly moves the ball bearing and the pocket to translate the collet to the proximal position and force the locking bearing proximally along the driveshaft to release the proximal end of the surgical tool.

In aspects according to the present disclosure, the distal end of the driveshaft includes a plurality of fork-like tines that cooperate in a spring-like manner to facilitate engagement with the proximal end of the tool shaft upon insertion thereof and wherein, upon rotation of the locking collar in the second direction and translation of the collet proximally, the plurality of fork-like tines facilitates release of the tool shaft from the driveshaft.

In aspects according to the present disclosure, the driveshaft is configured to releasably secure the tool shaft within the housing utilizing mechanically cooperating components including snap-fit members, keyed members, push-fit members, tongue and groove members, screw-fit members, and ball and socket members.

Provided in accordance with the present disclosure is a surgical device for cutting or shaving bone or tissue and includes a housing having an elongated tube extending therefrom and configured to receive the shaft of a surgical tool therein such that a length of the distal end of the surgical tool remains exposed, the elongated tube including a pocket defined therein configured to secure a portion of a ball bearing therein. A tool exposure mechanism is disposed about the elongated tube and is rotatably attached to a distal end of the housing, the tool exposure mechanism including a helical groove defined therein and extending therealong, the helical groove configured to receive an opposite end of the ball bearing. The tool exposure mechanism is rotatable in a first direction to move the ball bearing along the helical groove which, in turn, correspondingly moves the ball bearing and the pocket to translate the elongated tube relative to the shaft of the surgical tool and control the amount of exposure of the distal end of the surgical tool in a first direction.

In aspects according to the present disclosure, rotation of the tool exposure mechanism in the opposite direction controls the amount of exposure of the distal end of the surgical tool in an opposite direction.

In aspects according to the present disclosure, the pocket is defined in a proximal end of the elongated tube.

In aspects according to the present disclosure, the surgical device further includes a gear assembly disposed within the housing having a driveshaft configured to drive the surgical tool, the gear assembly selectively moveable between an oscillation mode and a rotation mode for driving the surgical tool.

In aspects according to the present disclosure, the surgical device further includes a motor operably coupled to the gear assembly, such that, upon activation thereof, the motor at least one of oscillates or rotates the surgical tool depending upon the position of the gear assembly.

Provided in accordance with the present disclosure is a surgical device for cutting or shaving bone or tissue and includes a housing configured to support a shaft of a surgical tool and a motor input. A gear assembly is disposed within the housing and is configured to drive the surgical tool. The gear assembly is operably engageable with a support chassis disposed within the housing. The support chassis is selectively moveable relative to the housing to switch the gear assembly between an oscillation mode wherein a transmission gear of the gear assembly engages a swing gear and a link of the gear assembly engaged with the motor input and a rotation mode wherein the transmission gear of the gear assembly engages a direct drive gear of the gear assembly engaged with the motor input.

In aspects according to the present disclosure, the support chassis is supported on a spring. In other aspects according to the present disclosure, the surgical device includes a guide plate disposed within the housing and configured to guide movement of the support chassis between modes. In yet other aspects according to the present disclosure, an outer ring is disposed about the housing and is configured to operably engage the guide plate, the outer ring is moveable to lock the guide plate relative to the housing in a selected operation mode. In still other aspects according to the present disclosure, the outer ring may be rotated or longitudinally displaced to lock the guide plate relative to the housing.

In aspects according to the present disclosure, the transmission gear is configured to disengage gears from a prior mode before engaging gears of the next mode.

In aspects according to the present disclosure, one or more of the gears of the gear assembly includes chamfered gear teeth to facilitate meshing with the other gears of the gear assembly during transition between modes. In other aspects according to the present disclosure, an angle of the chamfer on the gear teeth is in the range of about 5 degrees to about 35 degrees.

Provided in accordance with the present disclosure is a surgical device for cutting or shaving bone or tissue and includes a housing configured to support a shaft of a surgical tool and a motor input. A gear assembly is disposed within the housing and is configured to drive the surgical tool. The gear assembly is operably engageable with a support chassis disposed within the housing. The support chassis is configured to support a pair of synchronization gears that toggle atop a spring to switch the gear assembly between an oscillation mode wherein a transmission gear of the gear assembly engages a swing gear and a link of the gear assembly engaged with the motor input and a rotation mode wherein the transmission gear of the gear assembly engages a direct drive gear of the gear assembly engaged with the motor input.

In aspects according to the present disclosure, the synchronization gears include proximally-facing blocker rings that are configured to mesh with respective distally-facing blocker rings disposed on the direct drive gear and the swing gear when moved into engagement therewith during the respective modes of engagement.

In aspects according to the present disclosure, the surgical device includes a guide plate disposed within the housing and configured to guide movement of the support chassis between modes. In yet other aspects according to the present disclosure, an outer ring is disposed about the housing and is configured to operably engage the guide plate, the outer ring is moveable to lock the guide plate relative to the housing in a selected operation mode. In still other aspects according to the present disclosure, the outer ring may be rotated or longitudinally displaced to lock the guide plate relative to the housing.

In aspects according to the present disclosure, the transmission gear is configured to disengage gears from a prior mode before engaging gears of the next mode.

In aspects according to the present disclosure, one or more of the gears of the gear assembly includes chamfered gear teeth to facilitate meshing with the other gears of the gear assembly during transition between modes. In other aspects according to the present disclosure, an angle of the chamfer on the gear teeth is in the range of about 5 degrees to about 35 degrees.

BRIEF DESCRIPTION OF THE DRAWINGS

In the drawings, where like numerals refer to like components throughout several views.

DETAILED DESCRIPTION

Figure 1:
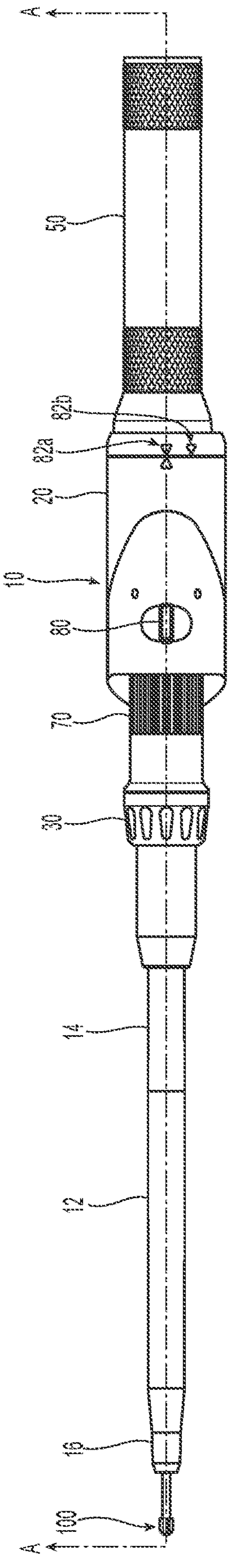
FIG. 1 is a top view of a cutting and shaving surgical device according to one embodiment of the present disclosure.
Figure 2:
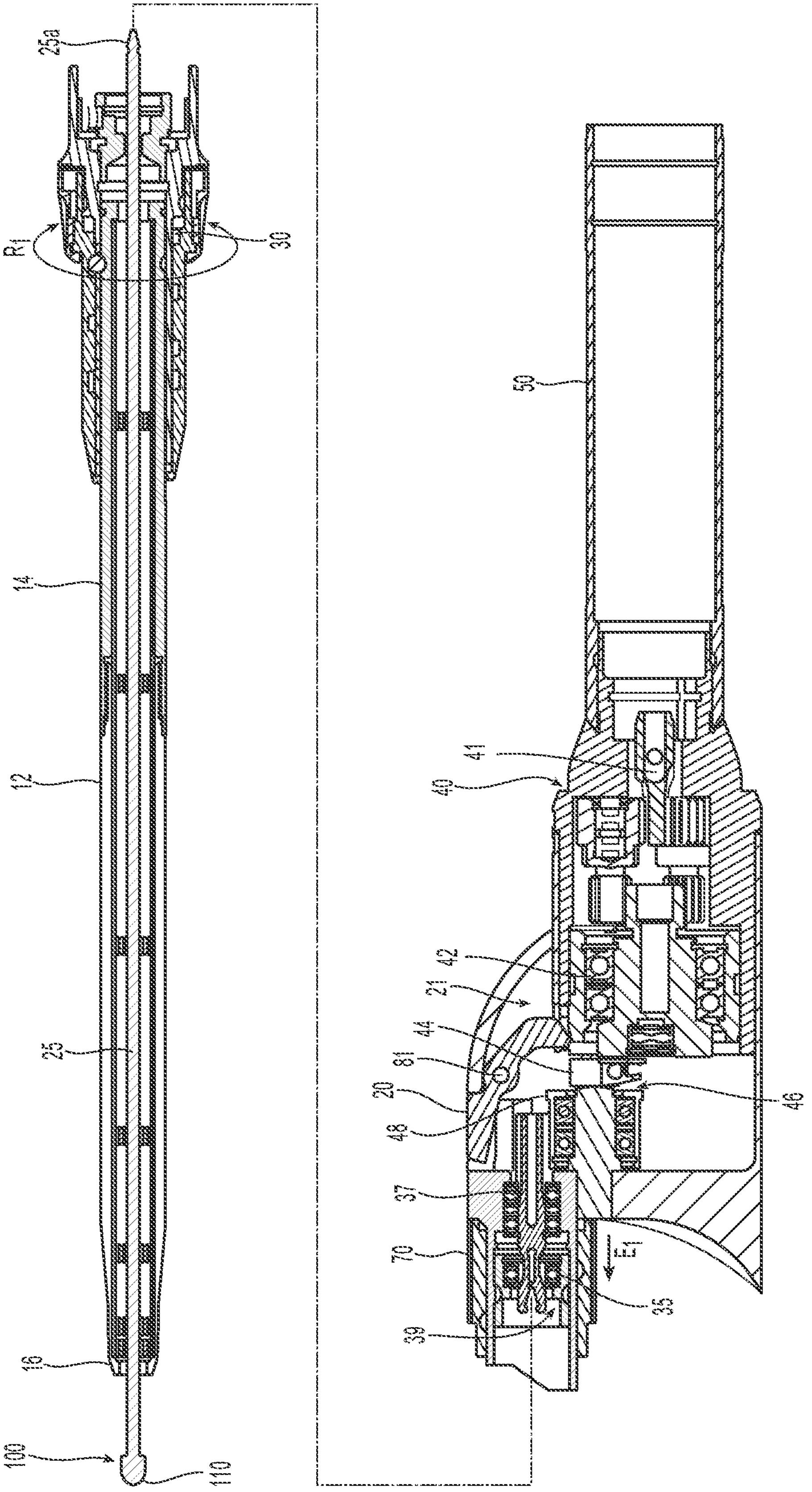
FIG. 2 is a side, cross sectional view of the cutting and shaving surgical device of FIG. 1 taken along line A-A of FIG. 1 showing a gear assembly disposed therein.
Figure 3:
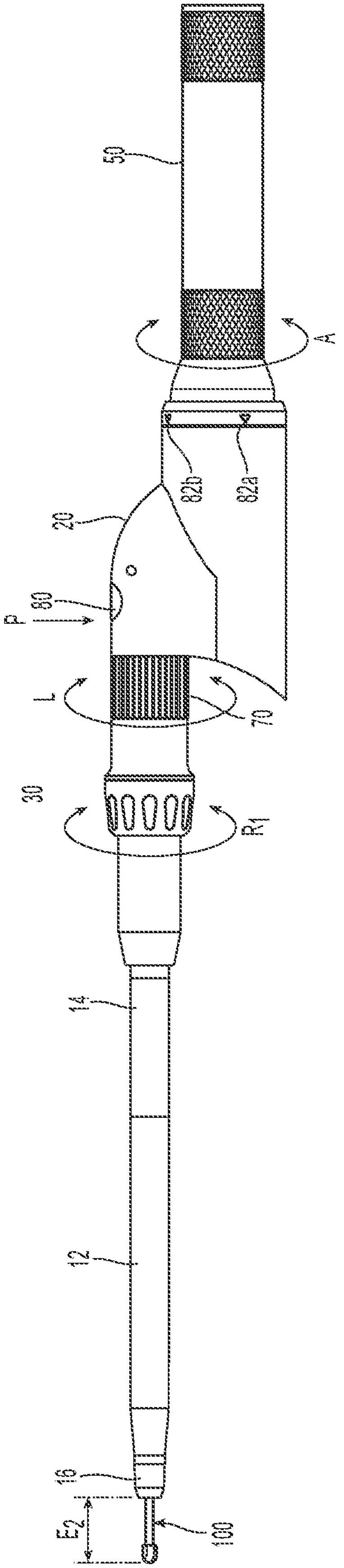
FIG. 3 is a side view of the cutting and shaving surgical device of FIG. 1.

FIGS. 1-3 illustrate one embodiment of a surgical device 10 configured for use in orthopedic and cranial surgical procedures for dissecting, cutting, shaving, and otherwise removing bone and hard tissue. Device 10 includes a housing 20 configured to be handled by a surgeon having a motor 50 operably associated therewith. Motor 50 may be ultimately connected to power source (not shown) or configured to house a battery (not shown) for portable use. Motor 50 is configured to operate at various speeds that may be controlled by a user via a speed dial or switch on the housing 20 or may be controlled at the power source. An elongated tube 12 extends from a distal end of the housing 20 and is configured to support a surgical tool 100, e.g., drill bit, dissecting head or bone shaver, at a distal end 16 thereof. A proximal end 14 of the tube 12 is removably engageable with the housing 20 and is lockable therein via a locking collet 70, a description of which is provided below. Elongated tube 12 may be configured to support the surgical tool 100 atop bearings (not shown) spaced therealong.

Housing 20 includes a cavity 21 defined therein configured to house a gear assembly 40 that operably engages the motor 50. More particularly, gear assembly 40 includes an input shaft 41 that is configured to operably engage a motor rotor shaft or collet (not shown) of the motor 50 (FIG. 2) such that rotational output of the rotor shaft correspondingly rotates the input shaft 41 at a 1:1 ratio. In embodiments, other gear ratios are contemplated. Input shaft 41 connects to a series of gears disposed within the housing 20 that cooperate to rotate a gear output shaft 42 at a desired speed (rotations per minute or RPM). Moreover, in certain integral systems, the rotor shaft of the motor 50 may be common and be the input gear 41 of the gear assembly 40.

The gear output shaft 42 couples to a link 44 that drives swing gear 48 such that the rotational output of the output shaft 42 is converted into oscillatory motion of the swing gear 48. The swing gear 48, in turn, couples to an oscillation converter 46 (which may include any known type of oscillation converter mechanism) that ultimately connect to a tool shaft 25 of the surgical tool at a proximal end thereof. Generally, the oscillation converter 46 is a subassembly of components that convert the rotary motion of the output gear 42 to oscillatory motion to move the tool shaft 25. In this instance, the subassembly of components includes the output gear 42, link 44, swing gear 48 and tool driveshaft 37.

The gear assembly 40 is selectively configurable to cooperate with one or more oscillation components 46 that may be selectively adjusted to vary the oscillation angle of the swing gear 48 as explained in more detail below with respect to FIG. 4D. More particularly, the housing 20 includes an angular displacement mechanism or lock 80 that is configured to selectively lock the motor 50 at one of a series of angular positions as denoted by indicia 82*a*-82*c* disposed thereon. Actuation of the lock 80 (e.g., pressing lock 80 into housing 20 in the direction "P") causes lock 80 to rotate about pivot 81 freeing the user to rotate the orientation of the motor 50 relative to housing 20 and gear assembly 40. As explained in more detail with respect to FIGS. 4A-4D, rotation of the motor 50 in the direction "A" reorientates the input shaft 41 and shaft 42 relative to the gear assembly 40 causing the gear assembly 40 to correspondingly rotate the swing angle of the swing gear 48 which, in turn, corresponds to the oscillation angle of the surgical tool 100 (e.g., drill bit). In embodiments, the swing angle of the swing gear relative to the oscillation angle may be a 1:1 ratio or a greater ratio depending upon a particular purpose. In embodiments, the ratio may be about 1:2. In other embodiments, the ratio may be about 1:3.5.

As mentioned above, a proximal end 25*a* of the tool shaft 25 is configured to selectively engage a collet 35 disposed within the housing 20 and operably associated with a locking collar 70. Locking collar 70 is rotatable between an open position which orients the collet 35 for selective receipt of the proximal end 25*a* of the tool shaft 25 and a locked position that engages the collet 35 onto the proximal end 25*a* of tool shaft 25. In embodiments, the proximal end 25*a* of the tool shaft 25 is keyed to facilitate engagement with the collet 35. The user simply rotates the locking collar 70 opposite the arrow "L" to load a tool shaft 25 and surgical tool thereon and then rotates the locking collar 70 in the reverse direction "L" to lockingly engage the tool shaft 25 within the collet 35. FIGS. 6E and 6F discuss details of an alternative locking collar 370. Collet 35 includes driveshaft 37 disposed on a proximal end thereof that is configured to mesh with the swing gear 48 such that oscillation of the swing gear 48 correspondingly oscillates the driveshaft 37, which, in turn, oscillates the tool shaft 25 when engaged.

Figure 4A:
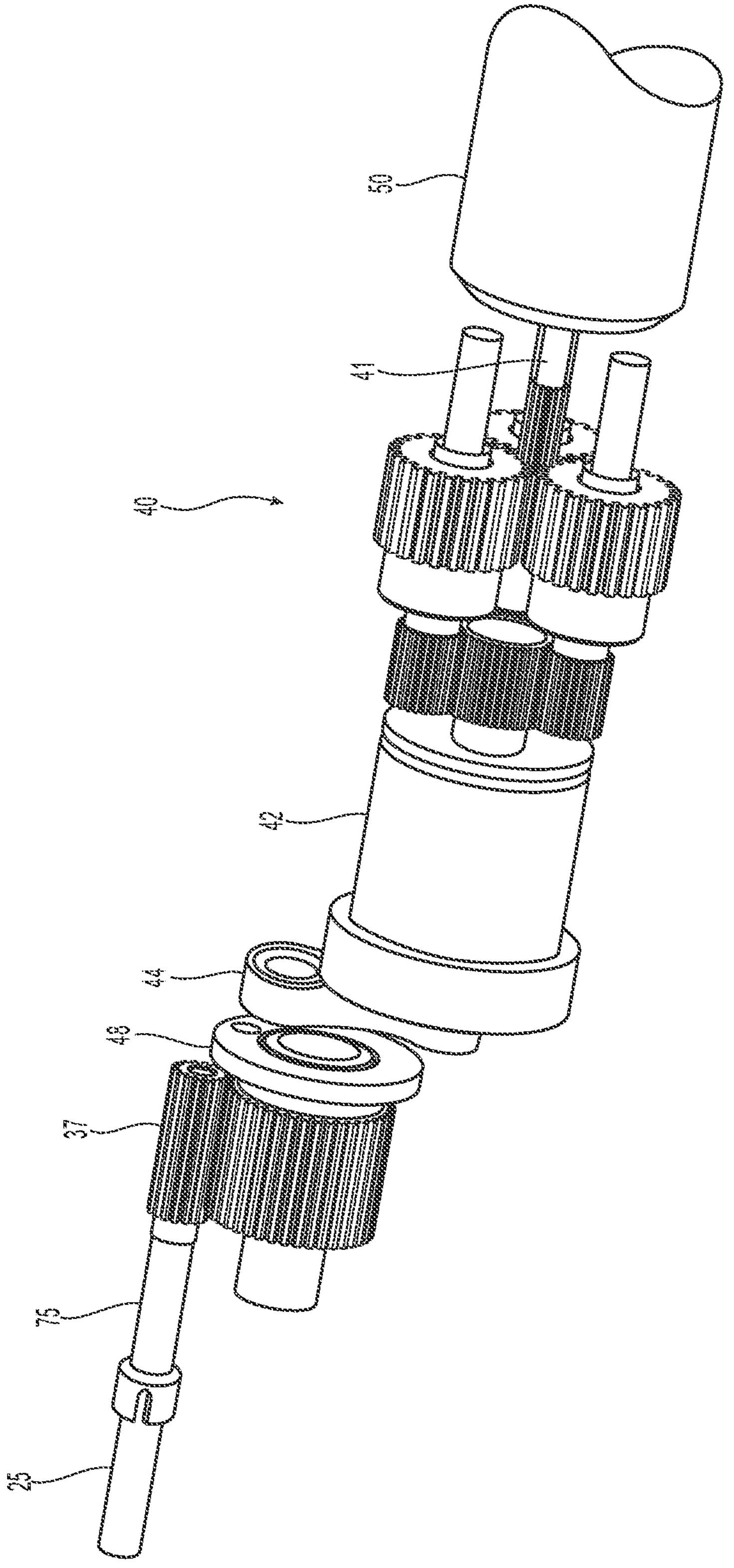
FIG. 4A is a rear, perspective view of a gear assembly and a motor of the cutting and shaving surgical device of FIG. 1.
Figure 4C:
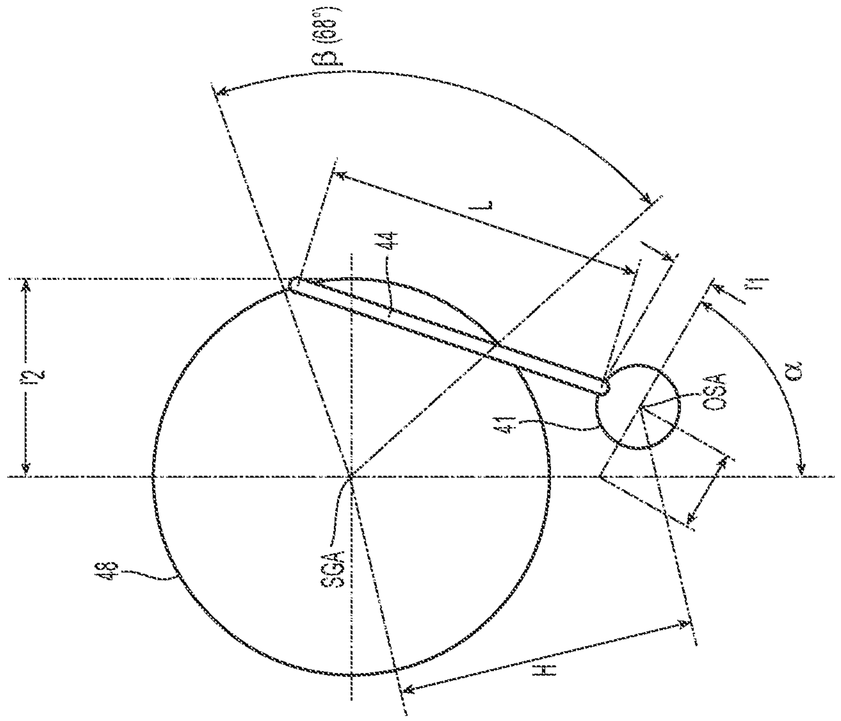
FIGS. 4B-4C are schematic views of a 4-Bar linkage diagram showing the angular displacement of the swing gear for two different gear configurations.
Figure 4B:
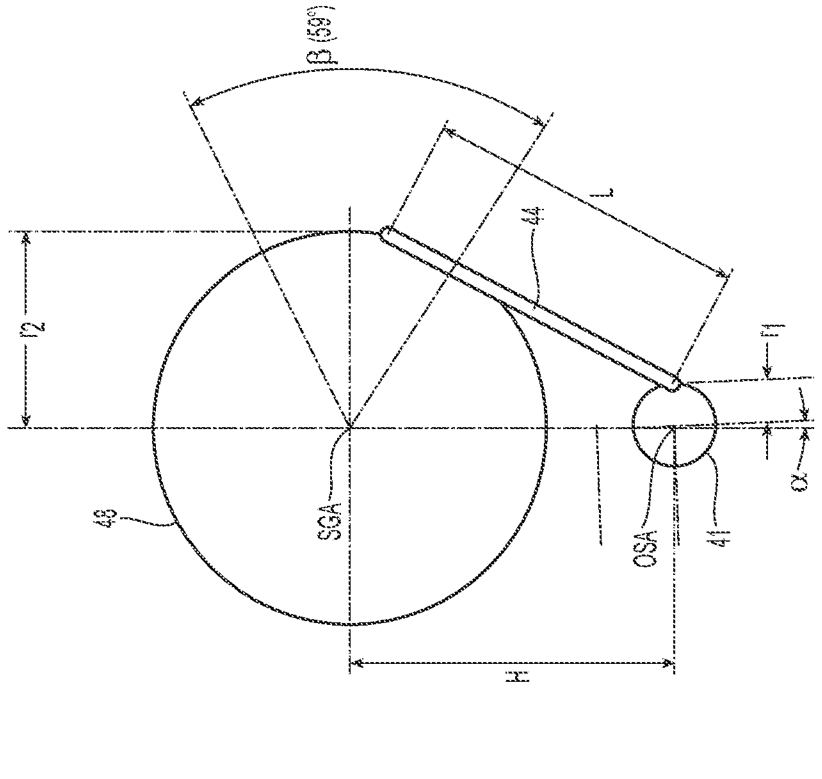
Figure 4D:
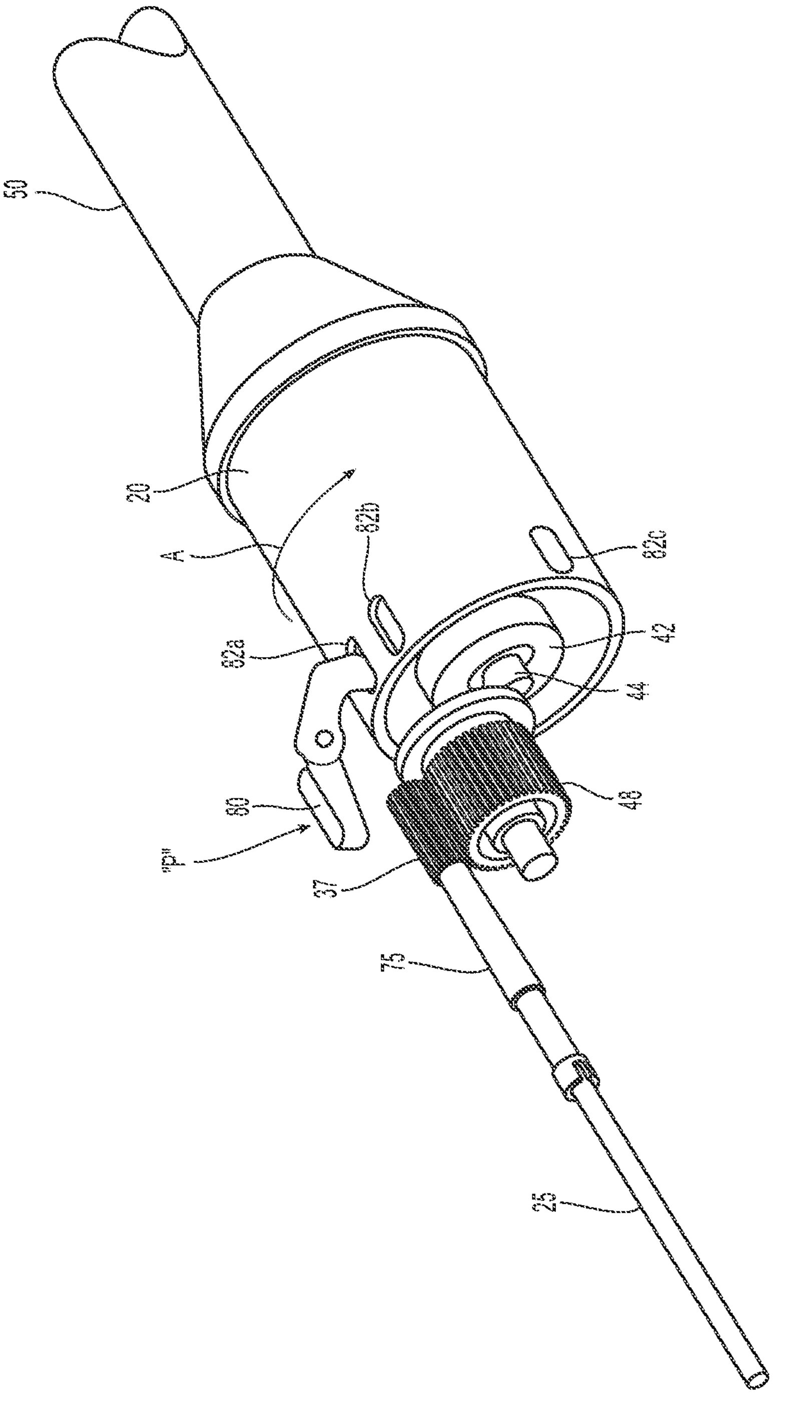
FIG. 4D is a front, perspective view of a gear housing moveable and lockable relative to the motor via an angular displacement locking mechanism.

Turning to FIGS. 4A-4D, FIG. 4A shows a rear perspective view of the input shaft 41 connected to the gear assembly 40 and the output shaft 42 and how the link 44 oscillates the swing gear 48 which, in turn, oscillates the tool shaft 25. FIG. 4B is a schematic representation of the mechanics behind the 4-Bar linkage assembly of the swing gear 48 and the angular travel of the swing gear 48 and relation of travel or angular displacement of the swing gear 48 as it relates to the position of the gear assembly housing 20. More particularly, and as mentioned above, the gear assembly housing 20 includes angular displacement lock 80 that is configured to selectively lock the motor 50 at one of a series of angular positions as denoted by indicia 82*a*-82*c* disposed thereon.

Oscillation of the swing gear 48 is based on the following factors as shown in FIG. 4B: the distance "H" between the swing gear axis SGA and the output shaft axis OSA; "L"—the link 44 length; "r1"—the distance from the link 44 connection to the center of the output shaft axis OSA; and "r2"—the distance from the link 44 connection to the center of the swing gear axis SGA.

Actuation of the lock 80 (e.g., pressing lock 80 into housing 20 in the direction "P") causes lock 80 to rotate about pivot 81 freeing the user to rotate the orientation of the motor 50 relative to gear assembly housing 20 and gear assembly 40. As shown in FIG. 4B this moves the center of the output shaft axis OSA and distance "H" effecting the angular displacement of the swing gear 48 as shown.

By comparison and, for example, FIG. 4B shows gear housing 20 with the lock 80 in position 82*c* wherein the swing gear 48 is at a minimum angular displacement (59°) and the motor output shaft axis OSA is in general registry with the swing gear axis SGA. Moreover, the distance "H" is at a maximum. When the user rotates the motor 50 to increase the angular displacement, for example to position 82*b*, the angular displacement of the motor output shaft axis OSA moves away from the swing gear axis SGA and the angle $\alpha$ gets greater (See FIG. 4C) coupled with the distance from the swing gear axis SGA to the output gear axis "H" getting smaller (See FIG. 4C). As a result, the swing gear total angular travel $\beta$ increases (68°). In position 82*a*, the motor 50 is rotated to a maximum angularly displaced orientation and the swing gear 48 is oscillating at a maximum angle. As mentioned herein, this allows the surgical tool 100 to cut more aggressively as explained in more detail below.

Housing 20 also supports a tool exposure mechanism 30 that is configured to regulate the length of exposure of the surgical tool 100 relative to the distal end 16 of the elongated tube 12. This provides the surgeon with additional flexibility when using the surgical device 10. More particularly and as best shown in FIG. 2, collet 35 is selectively moveable within a cavity 39 defined in housing 20. Rotation of the tool exposure mechanism 30 in a counter-clockwise direction "R1" correspondingly moves the collet 35 within the cavity 39 a distance of "E1". Movement of the collet 35 in a direction "E1", in turn, exposes the surgical tool 100 a corresponding distance "E2" from the distal end 16 of the elongated tub 12. In embodiments, "E1" and "E2" may be equivalent or in other embodiments, "E1" and "E2" may be different and movable subject to a specific gear ratio. Rotation of the tool exposure mechanism 30 in the opposite direction will retract the surgical tool 100 within the distal end 16. In embodiments, other types of actuators are contemplated, e.g., a slide actuator, a toggle, etc. FIGS. 6C and 6D discussed below discuss an alternate embodiment of a tool exposure mechanism 330 wherein internal components of the elongated tube are configured to slide relative to the driveshaft to regulate tool exposure.

In use, a surgeon initially loads a surgical tool 100 drive shaft 25 into the housing 20 of device 10 by rotating lock 70 in a counter-clockwise direction (opposite direction of "L") to open collet 35. Once open, the surgeon slides the shaft 25 within elongated tube 12 such that the proximal end 25*a* of the shaft 25 bottoms out into the collet 35 or otherwise engages the collet 35. The surgeon then rotates the lock 70 in the opposite direction "L" to close the collet 35 onto the proximal end 25*a* and lock the tool shaft 25 within device 10. Once locked, the device 10 is ready for use.

If a surgeon wants to change the angular displacement of the oscillation of the surgical tool 100 for a particular surgical purpose, e.g., adjust the aggressiveness (finer cutting or more aggressive cutting) of the surgical tool 100, the surgeon simply depresses the angular displacement lock 80 and rotates the motor 50 relative to the housing 20. As mentioned above, rotation of the motor 50 correspondingly adjusts one or more gears of the gear assembly 40 which, in turn, adjusts the swing angle of the swing gear 48 effecting the angle of oscillation of the surgical tool 100.

Additionally, if a surgeon wants to change the exposure length "E2" of surgical tool 100 for a particular surgical purpose, e.g., better control, visibility or depth of plunge, the surgeon simply rotates the tool exposure mechanism 30 to move collet 35 which, in turn, extends or retracts the exposure length "E2" of the surgical tool 100 relative to the distal end 16 of the elongated tube 12.

Figure 5C:
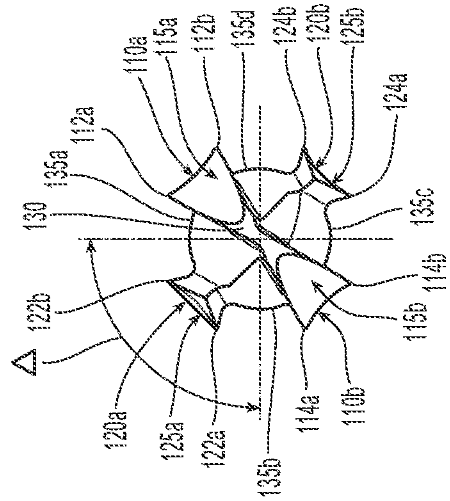
FIGS. 5A-5C are various enlarged views of a surgical tool for use with embodiments of the cutting and shaving surgical devices described herein.
Figure 5A:
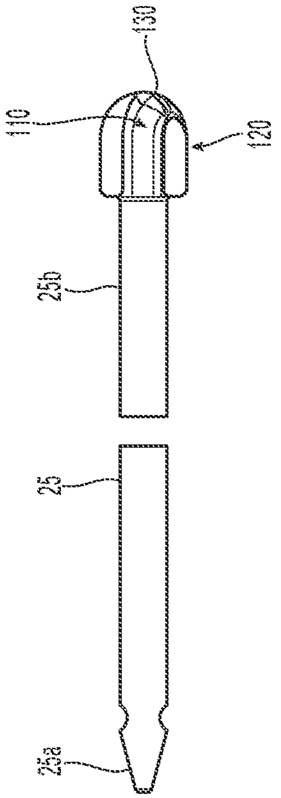
Figure 5B:
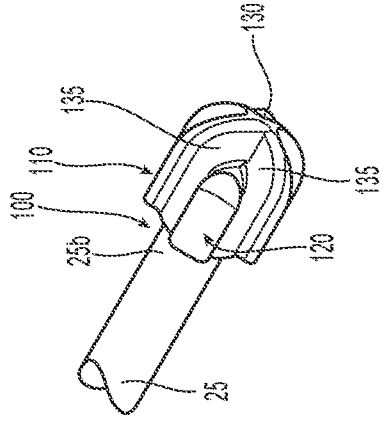

Turning to FIGS. 5A-5C which show various views of the surgical tool 100, which, in this particular case, is shown a drill bit that may be used for both plunge-cutting into bone or hard tissue and shaving. More particularly, surgical tool 100 (hereinafter "drill bit 100") is disposed at the distal end 25*b* of the drive shaft 25 and includes a series of cutting flutes disposed therearound, generally identified as flutes 110 and 120, as well as a cutting tip 130 at a distal-most end thereof. Generally, cutting tip 130 facilitates plunge-cutting into bone or hard tissue while flutes 110 and 120 facilitate shaving. However, the flutes 110 and 120 and cutting tip 130 may each be configured to facilitate both cutting and shaving depending upon a particular purpose.

Drill bit 100 includes two pairs of opposing flutes, namely, flutes 110*a*, 110*b* and flutes 120*a*, 120*b*. Any number of cutting flutes may be employed, but for the purposes herein, flutes are described as a pair of flutes 110*a*, 110*b*. Flutes 110*a*, 110*b* are generally larger than flutes 120*a*, 120*b* and converge to form cutting tip 130 at a distal end thereof. Flute 110*a* includes a deep groove 115*a* defined between opposing cutting edges 112*a*, 112*b* which, when the drill bit 100 is oscillating, facilitates removal of the bone fragments. Flute 110*b* includes similar elements on the opposing side of the drill bit 100, namely, groove 115*b* defined between cutting edges 114*a*, 114*b*. Flutes 110*a*, 110*b* and the cutting tip 130 cooperate to facilitate plunge-cutting into bone or hard tissue. The cutting edges 112*a*, 112*b* and 114*a*, 114*b* of flutes 110*a*, 110*b* are also configured to cooperate with flutes 120*a*, 120*b* to facilitate shaving or side cutting.

Flutes 120*a* includes a deep groove 125*a* defined between opposing cutting edges 122*a*, 122*b* which, when the drill bit 100 is oscillating, facilitates removal of the bone fragments when shaving. Flute 120*b* includes similar elements on the opposing side of the drill bit 100, namely, groove 125*b* defined between cutting edges 124*a*, 124*b*. Sections 135*a*-135*d* are defined between adjacent flutes, e.g., section 135*a* is defined between flute 110*a* and flute 120*a* and are configured to facilitate removal as well. Sections 135*a*-135*d* are also configured to facilitate the removal of bone or tissue during both plunge-cutting and shaving.

In contrast to rotational cutting which generally requires a single leading cutting edge to cut bone as the rotational cutting tool rotates in a single direction, the drill bit 100 of the present disclosure includes two edges on opposite sides of the groove 115*a* which provide a leading cutting edge during clockwise rotation, e.g., cutting edge 112*b*, and a leading cutting edge during counter-clockwise rotation, e.g., cutting edge 112*a*. This enhances plunge-cutting with the larger flutes 110, 110*b*. Similarly, flutes 120*a*, 120*b* each include opposing cutting edges, e.g., edges 114*a*, 114*b*, which act as leading edges for bone and tissue shaving.

By adjusting the oscillation angle via actuating the angular adjust lock 80 and rotating the motor 50, a surgeon can opt for a greater oscillation angle Δ for more aggressive cutting or a lower oscillation angle Δ for finer cutting. In embodiments, the drill bit 100 may be keyed (or configured to allow insertion in only one orientation). Changing the drill bit 100 oscillation angle Δ without changing the speed of the motor 50 will alter the cutting performance of the drill bit 100. For example, if the oscillation angle Δ is increased the drill bit 100 will rotationally travel faster and further which increases the number of flutes cutting bone. Likewise, if the oscillation angle Δ is decreased, the drill bit 100 will rotationally travel slower and less radial distance which reduces the number of flutes cutting bone.

FIGS. 6A-14 illustrate another embodiment of a surgical device 300 configured for use in orthopedic and cranial surgical procedures for dissecting, cutting, shaving, and otherwise removing bone and hard tissue. Surgical device 300 and surgical device 10 are generally similar in certain respects with the exception that surgical device 300 has the additional capability of a rotational mode for the drill bit 100 when the drive gear housing 390 is moved to a rotational mode position as explained in more detail below. For the purposes of brevity, certain aspects of the surgical device 300 are not explained in detail with the understanding that these aspects are similar to surgical device 10.

Figure 6A:
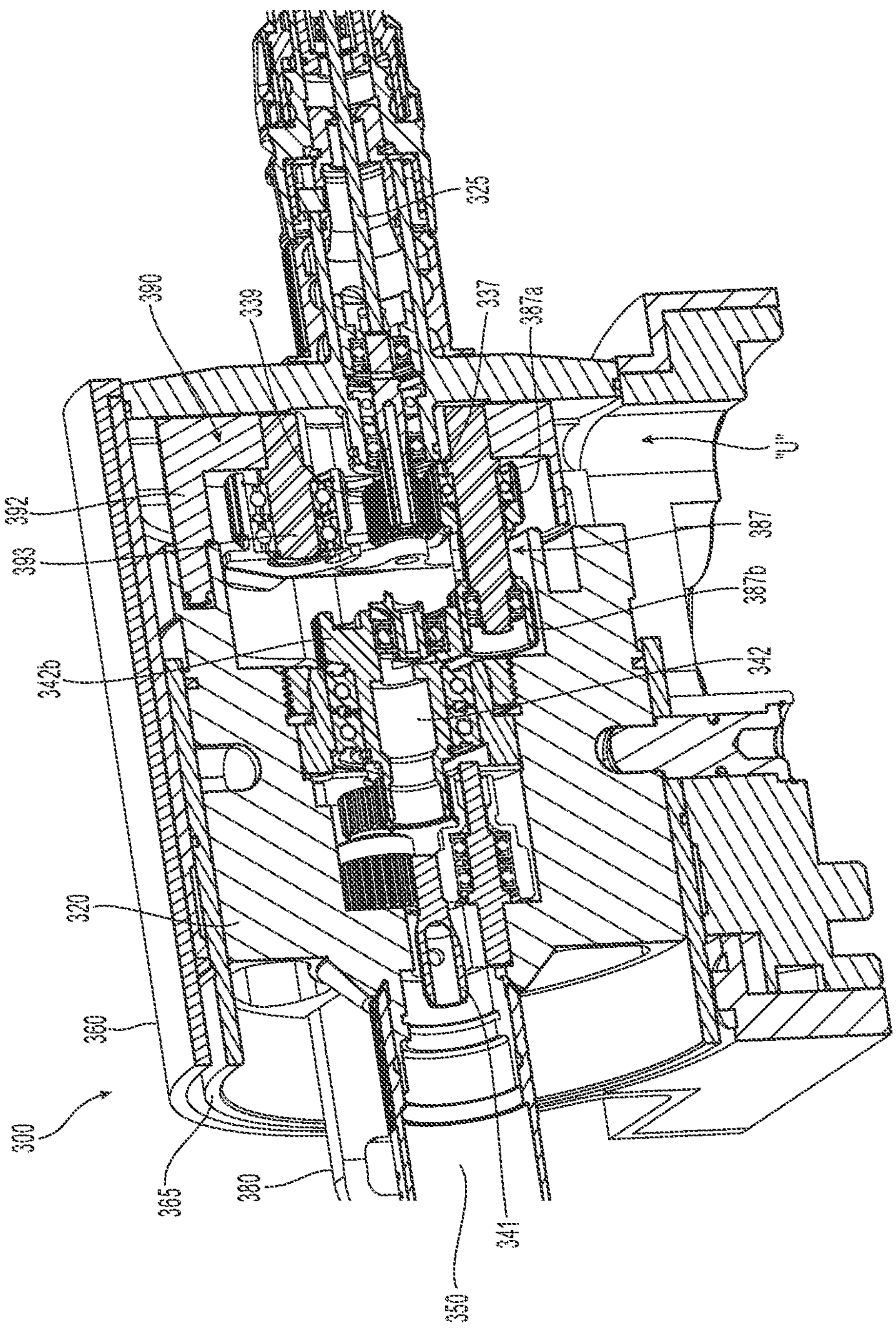
FIG. 6A is an internal cross-sectional view of a cutting and shaving surgical device according to another embodiment of the present disclosure capable of both rotation and oscillation of a surgical tool with a single drive gear.
Figure 6B:
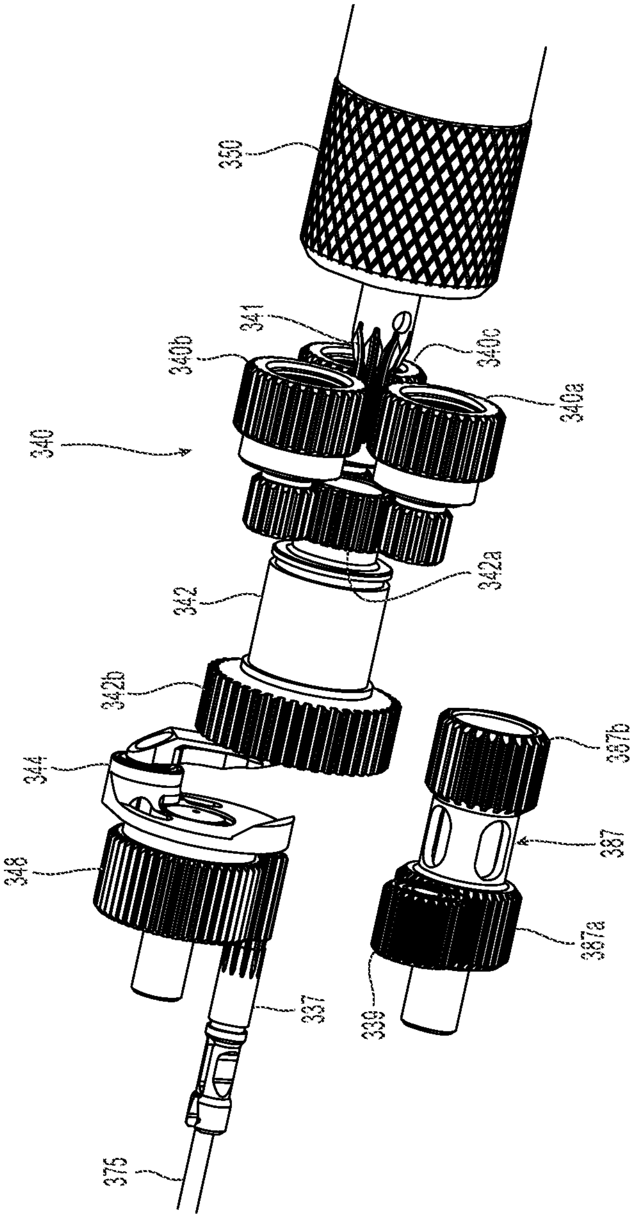
FIG. 6B is a rear, perspective view of an internal gear arrangement of the surgical device of FIGS. 6A and 7A-14 and a motor disposed in an oscillation mode.
Figure 6C:
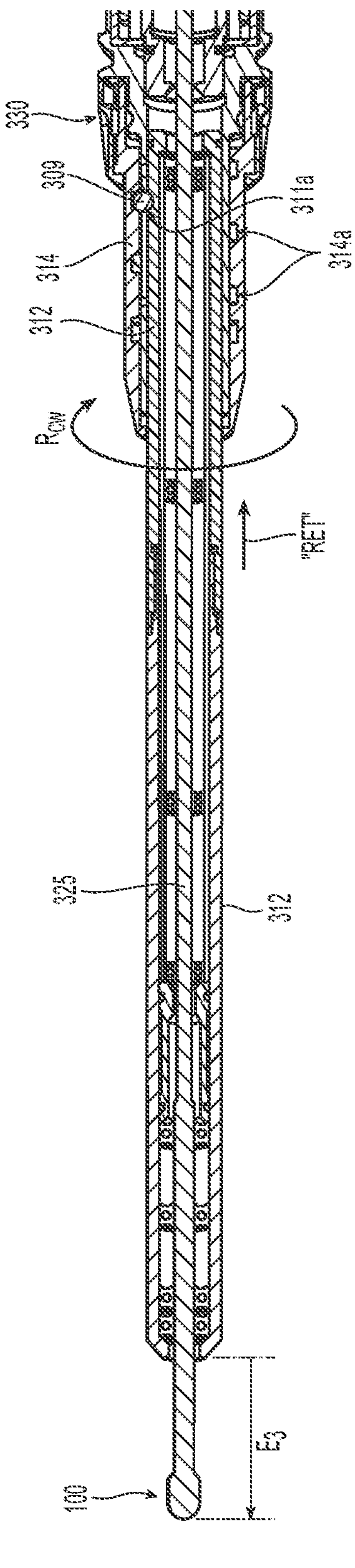
FIGS. 6C-6D are side, cross-sectional views of the surgical device of FIGS. 6A and 6B illustrating an alternate embodiment of a tool exposure mechanism in various positions of exposure.
Figure 6D:
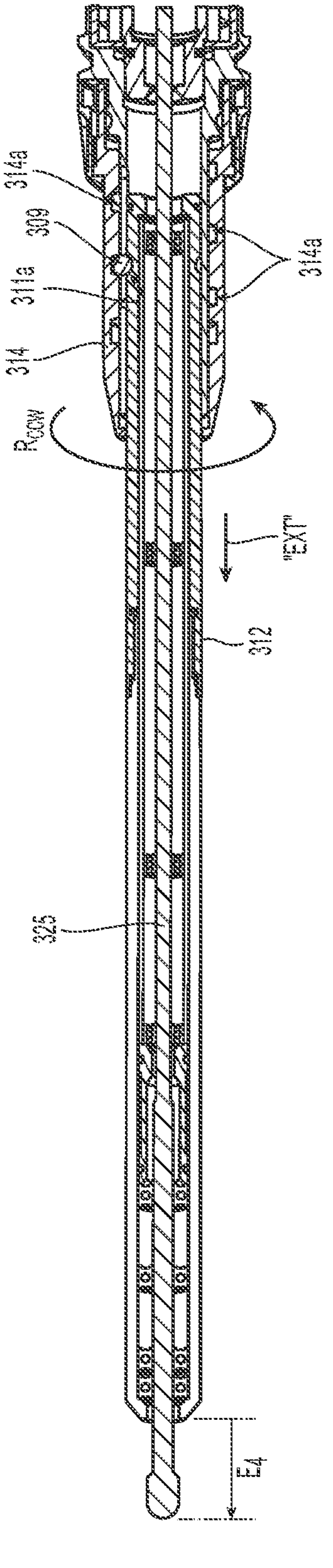
Figure 6E:
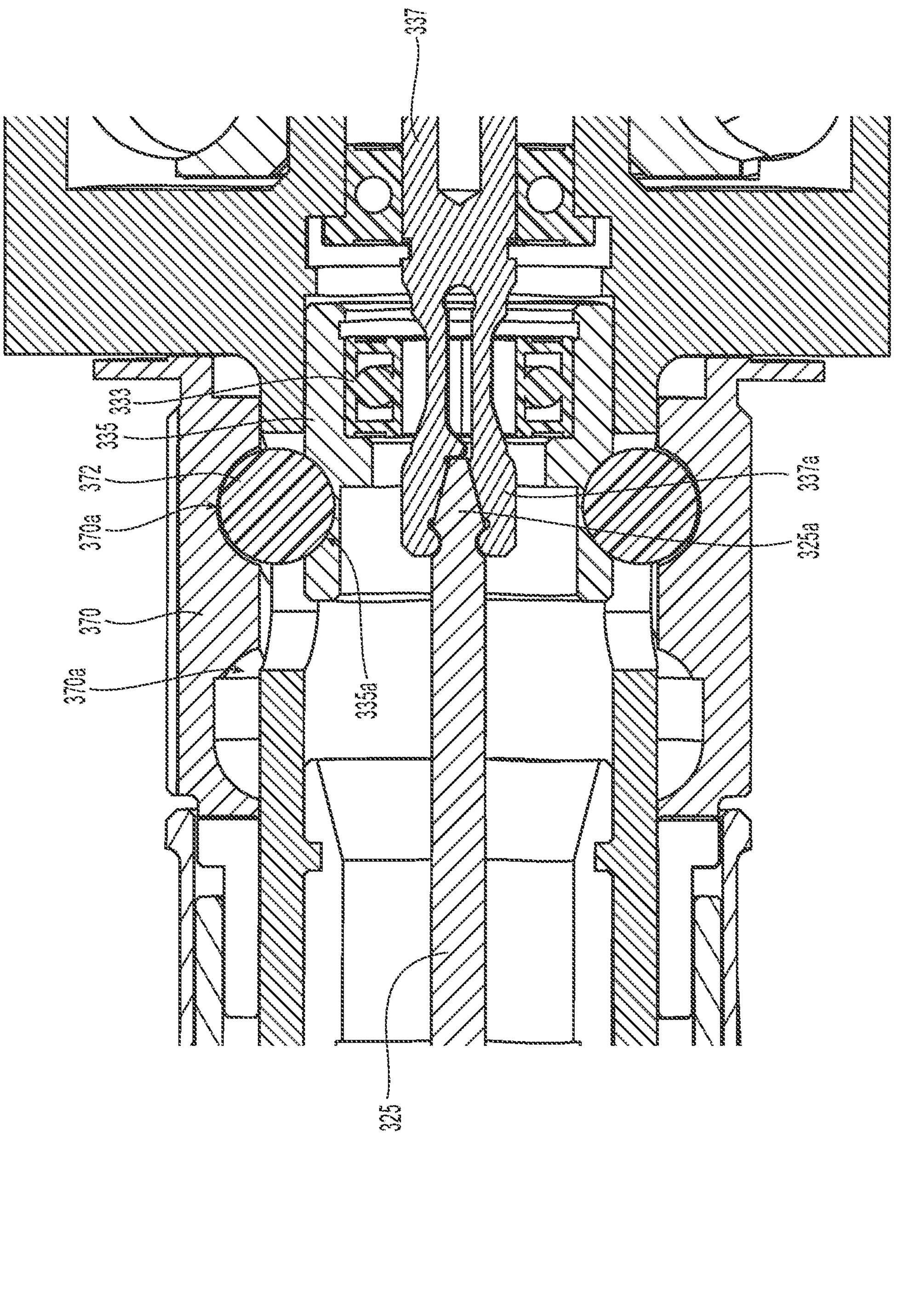
FIGS. 6E-6F are side, cross-sectional views of the surgical device of FIGS. 6A and 6B illustrating an alternate embodiment of a locking collar in various positions of engagement.
Figure 6F:
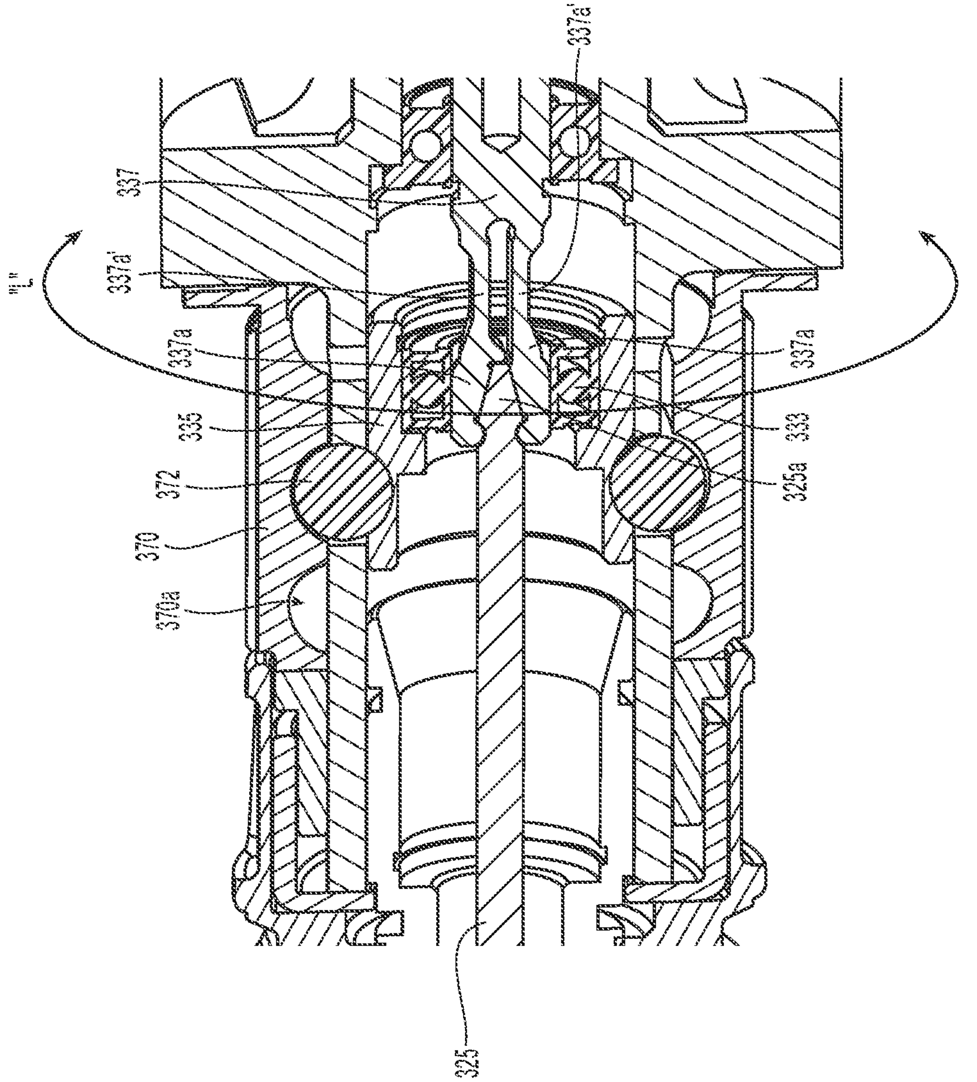

Turning initially to FIGS. 6A-6B which show the surgical device 300 which includes an outer housing 360 configured to be mounted on a surgical robot and/or controlled by a surgeon having a motor 350 operably associated therewith. Motor 350 may be ultimately connected to power source (not shown) or configured to house a battery (not shown) for portable use. Motor 350 is configured to operate at various speeds that may be controlled by a user via a speed dial or switch on the housing 320 or may be controlled at the power source. An elongated tube 312 extends from a distal end of the housing 320 and is configured to support a surgical tool, e.g., drill bit 100, dissecting head or bone shaver, at a distal end 16 thereof as described in detail above with respect to FIGS. 1-5C. A proximal end 314 of the tube 312 is removably engageable with the housing 320 and is lockable therein when the drill bit 100 is locked via a locking collet 370, again in a similar manner as described above.

Housing 320 is configured to house a gear assembly 340 that operably engages the motor 350. More particularly, gear assembly 340 includes an input shaft 341 that is configured to operably engage a rotor shaft or collet (not shown) of the motor 350 such that rotational output of the output gear correspondingly rotates the input shaft 341 at a 1:1 ratio. Moreover, in certain vernaculars, the output gear of the motor 350 may be commonly referred to as the input gear 341 of the gear assembly 340. In embodiments, other gear ratios are contemplated. Input shaft 341 connects to a series of gears 340*a*-340*c* disposed within the housing 320 that cooperate to rotate a gear output shaft 342 at a desired speed (rotations per minute or RPM).

The gear output shaft 342 includes a distal end 342*a* that couples to a link 344 that drives swing gear 348 such that the rotational output of the output shaft 342 is converted into oscillatory motion of the swing gear 348. In other words, the rotational motion of the distal end 342*a* of the output shaft 342 moves the link 344 in a general vertically arcuate motion (See, e.g., FIGS. 4B and 4C) which, in turn, oscillates the swing gear 348 and, ultimately, tool shaft 325. As explained in more detail below, both the swing gear 348 used for oscillation mode a direct drive gear 387 and idler gear 339 (FIG. 14) used for rotational mode are housed in a selectively moveable drive gear housing 390. When disposed in the oscillation mode, swing gear 348 meshingly engages the proximal end gear or drive shaft 337 and when disposed in the rotational mode, the idler gear 339 meshingly engages the proximal end gear of drive shaft 337.

The gear assembly 340 is selectively configurable to cooperate with one or more oscillation components that may be selectively adjusted to vary the oscillation angle of the swing gear 348 as explained in more detail below. More particularly, the housing 320 includes a collet housing 365 secured to an inner peripheral surface thereof that defines a series of apertures 382*a*-382*c* circumferentially spaced thereabout (FIG. 7B). Similar to device 10, an angular displacement or lever lock 380 enables a user to rotate the housing 320 relative to the motor 350 (or vice versa) and lock the housing 20 at various angular positions within apertures 382*a*-382*c* relative to the motor 350.

Actuation of the lever lock 380 (e.g., pressing lock 380 into or towards the housing 320 against the bias of spring 387 about a pivot 381 (FIG. 9)) causes lever lock 380 to rotate freeing the user to rotate the orientation of the housing 320 and gear assembly 340 relative to the motor 350. As explained above with respect to FIGS. 4A-4D and, also, with particular respect to FIG. 8B, when the distance between the axis SGA of the swing gear 348 and the axis OSA of the input gear 341 is reduced (in other words the distance "H" in FIG. 8B), the oscillation angle β is increased.

Figure 7A:
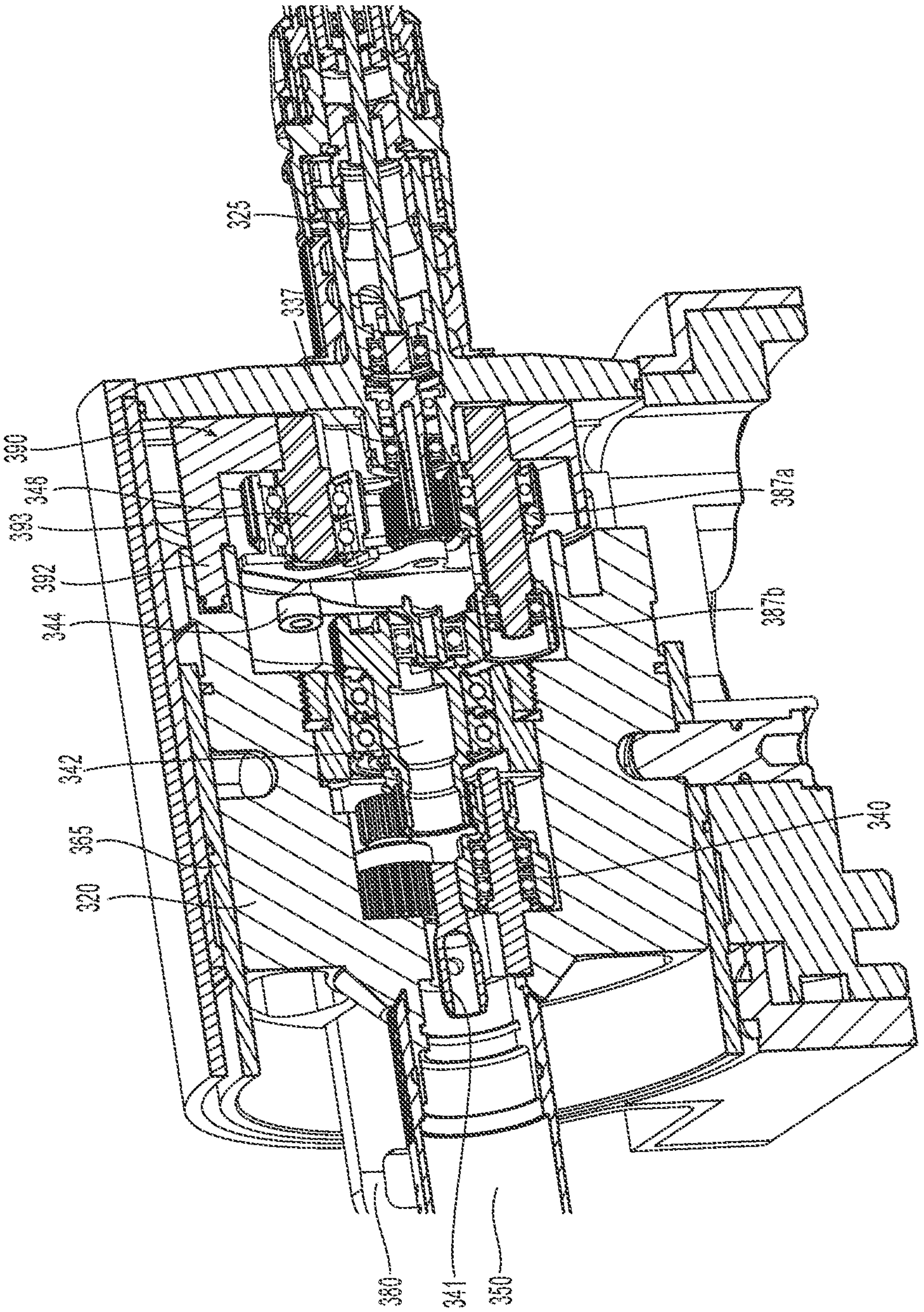
FIG. 7A is an internal cross-sectional view of the cutting and shaving surgical device of FIG. 6A wherein the internal gear assembly is disposed in a first configuration resulting in a first oscillation angle for the surgical tool.
Figure 7B:
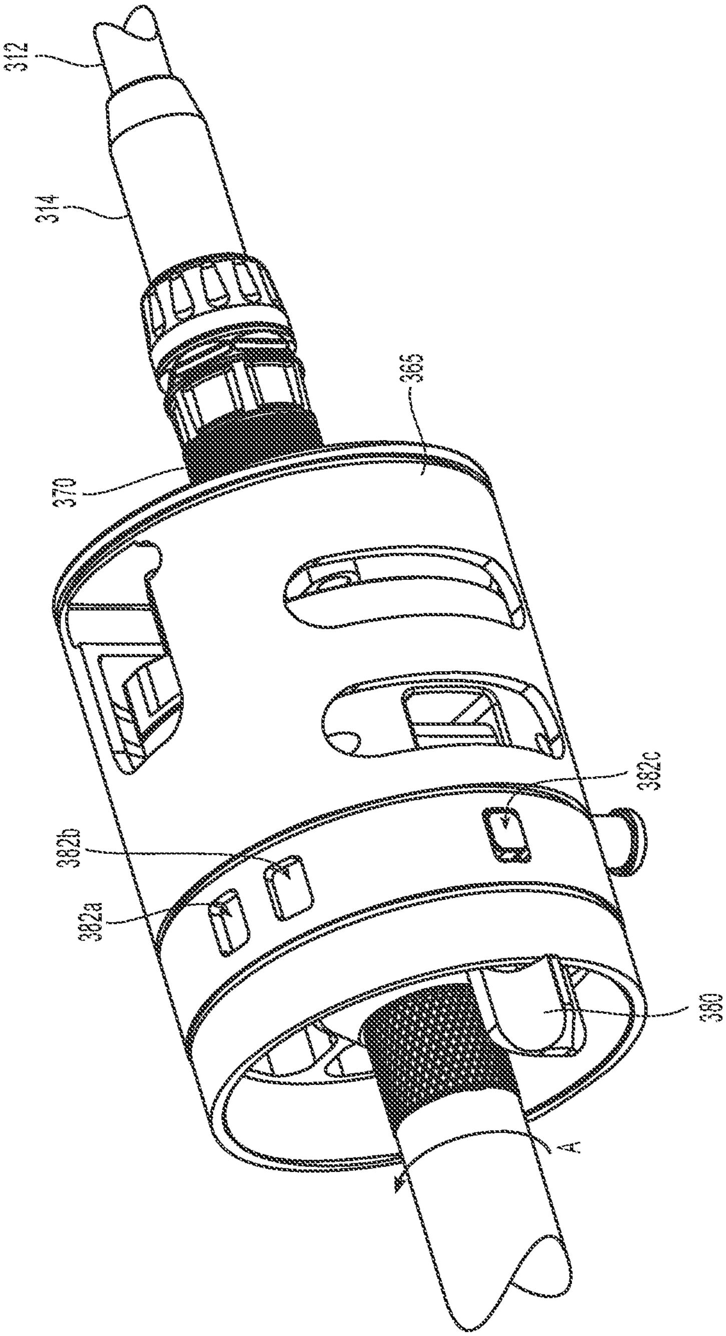
FIG. 7B is a rear perspective view of a collet configured to lock the gear assembly relative when rotated relative thereto at one or more angular positions by a lever lock.

Turning now to the various angular displacement configurations as shown in FIGS. 7A-9, as mentioned above, lever lock 380 is depressible in the direction "P" about the pivot 381 (FIG. 9) to allow movement of the housing 320 in the direction of arrow "A" relative to the motor 350 which, in turn, reorients the distance between the axes of the motor 350 and the swing gear 348 thereby increasing the swing angle β of the link 344. FIGS. 7A and 7B show the surgical device 300 in an oscillation mode with the lever lock 380 in a first angularly displaced position. Once the lever 380 is properly aligned within the selected aperture, e.g., aperture 382*c*, the lever lock 380 is released and under the bias of a spring 387 (FIG. 9) returns the lever lock 380 to engage the aperture 382*c* which locks the housing 320 relative to the motor 350 at the first angularly displaced position. Upon activation of the motor 350, and as explained in detail above, the gear assembly 340 and the link 344 cooperate to oscillate the swing gear 348 at a specific oscillation rotation angle β which, in turn, oscillates the drill bit 100 at a corresponding oscillation rotational angle Δ. In this particular instance, at the first angularly displaced position the swing gear oscillation rotational angle β may be in the range of about 48° to about 64° degrees.

It is important to note that during activation of the motor 350, the axis OSA of rotation of the input gear 341 relative to the axis SGA of rotation swing gear 348 although parallel are not coincident. As mentioned above, the two axes are offset the distance "H" relative to one another and as the distance "H" changes the swing angle β changes (See, e.g., FIGS. 4A, 4B and 8B).

Figure 8A:
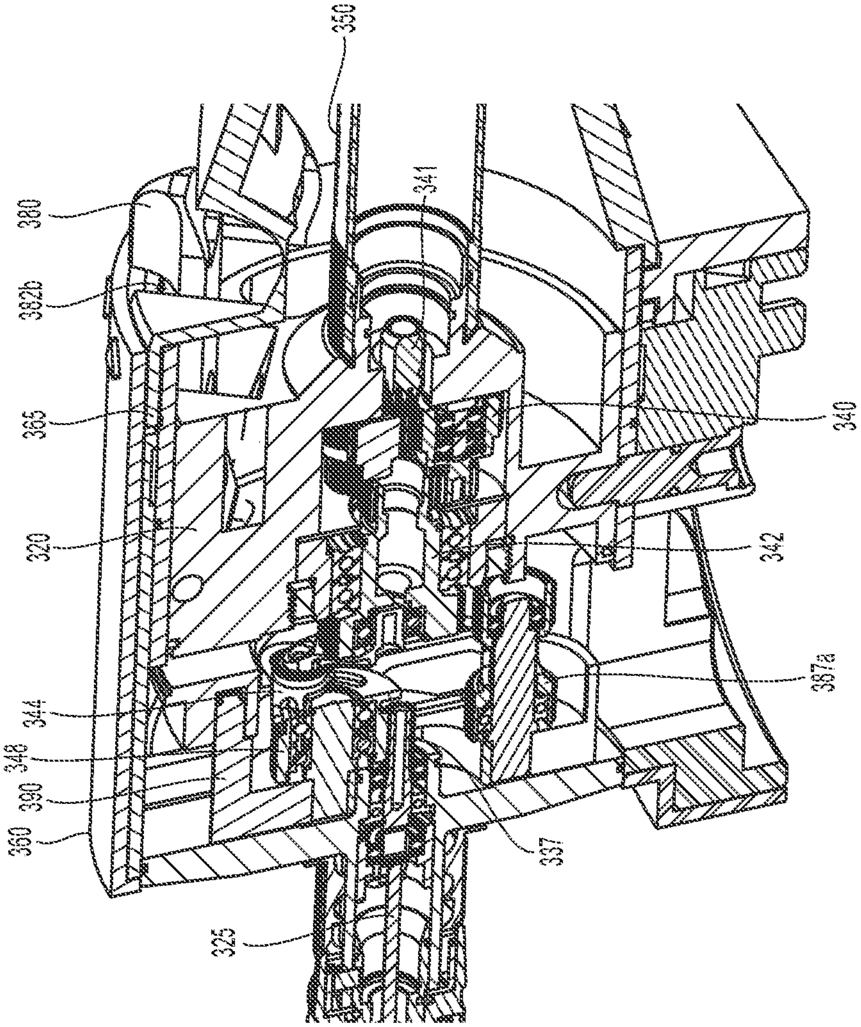
FIG. 8A is an internal cross-sectional view of the cutting and shaving surgical device of FIG. 6A wherein the gear assembly is disposed in a second configuration resulting in a second oscillation angle for the surgical tool.
Figure 8B:
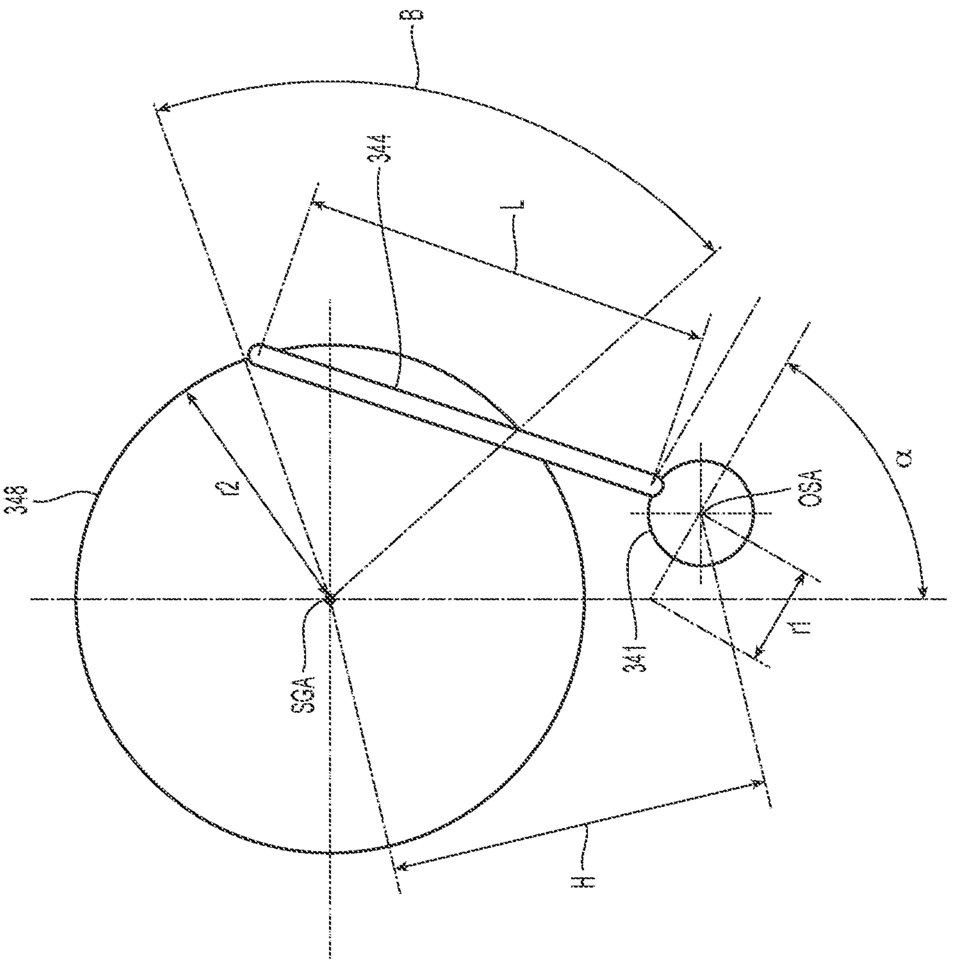
FIG. 8B is a schematic view of a 4-Bar linkage diagram showing the angular displacement of a swing gear for the gear assembly in the second configuration.

If it is desirous to utilize the drill bit 100 in a more aggressive manner to shave bone or tissue, the surgeon may opt to increase the oscillation angle β further by rotating the housing 320 to the second angularly displaced position as shown in FIGS. 8A and 8B. In a similar manner to FIGS. 7A and 7B described above, the lever lock 780 is depressed about pivot 381 (FIG. 9) against the bias of spring 387 to allow the surgeon to rotate and reorient the housing 320 to the second angularly displaced position and then release the lever lock 380 to lock within aperture 382*b*. Upon activation of the motor 350, the gear assembly 340 and the link 344 cooperate to oscillate the swing gear 348 at a specific oscillation rotation angle β which, in turn, oscillates the drill bit 100 at a corresponding oscillation rotational angle Δ. In this particular instance, at the second angularly displaced position the swing gear oscillation rotational angle β may be in the range of about 65° to about 72° degrees.

As noted above and as shown in the comparison of FIGS. 4A and 4B (which is similar to FIG. 8B but for surgical device 300), as a result of the movement of the lever lock 380 from the first angularly displaced position to the second angularly displaced position the distance "H" between the axis OSA and the axis SGA changed (decreased) resulting in a change in the swing angle θ of the swing gear 348 (increase).

Figure 9:
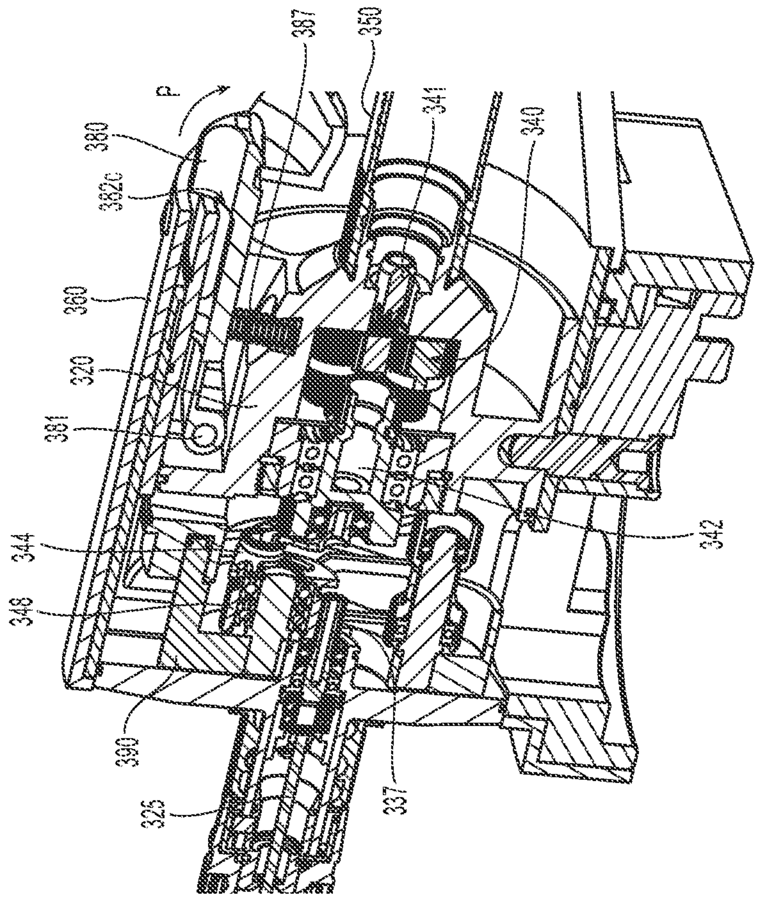
FIG. 9 is an internal, cross-sectional view of the cutting and shaving surgical device of FIG. 6A wherein the gear assembly is disposed in a third configuration resulting in a third, maximum oscillation angle for the surgical tool.
Figure 10:
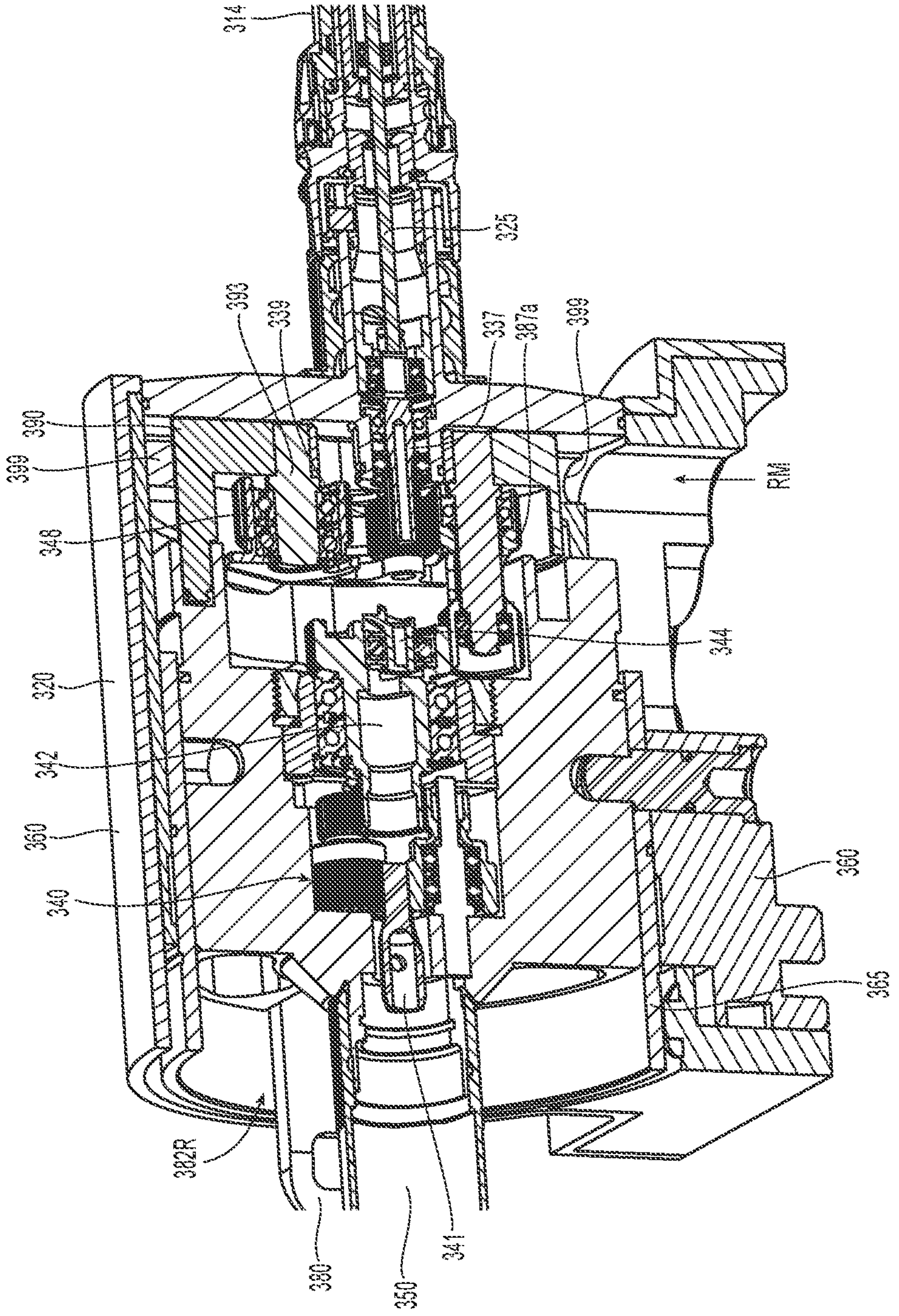
FIG. 10 is an internal cross-sectional view of the cutting and shaving surgical device of FIG. 6A wherein a drive gear housing moves the drive gear assembly to a rotational mode while at the same time disengaging the oscillation mode.

If a surgeon wishes to maximize the cutting effectiveness of the drill bit 100 for shaving purposes and use the drill bit 100 in the most aggressively-designed manner to shave bone or tissue, or perhaps to plunge the drill bit 100 into bone or tissue, the surgeon may opt to increase the oscillation angle θ further by rotating the housing 320 to the last angularly displaced position intended for oscillation of the drill bit 100 as shown in FIG. 9. In a similar manner to FIGS. 7A, 7B and 8A, 8B described above, the lever lock 380 is depressed about pivot 381 (FIG. 9) against the bias of spring 387 to allow the surgeon to rotate and reorient the housing 320 to the last angularly displaced position intended for oscillation motion of the drill bit 100 and then release the lever lock 380 to within aperture 382*a*. Upon activation of the motor 350, the gear assembly 340 and the link 344 cooperate to oscillate the swing gear 348 at a specific oscillation rotation angle β which, in turn, oscillates the drill bit 100 at a corresponding oscillation rotational angle Δ. In this particular instance, at the last angularly displaced position the swing gear oscillation rotational angle β is configured to be in the range of about 73° to about 85° degrees or an intended maximum anticipated design which, in embodiments, may be dependent upon the drill bit 100.

As noted above, the change in distance "H" between the axis OSA of the motor 350 and the axis SGA of the swing gear 348 effects a change in the swing angle β of the swing gear 348 which, in turn, effects the change in the corresponding oscillation rotational angle Δ of the drill bit 100. In embodiments, the gear ratio between the gear of the drive shaft 337 and the swing gear 348 used to drive the surgical tool, e.g., drill bit 100, may be in the range of about 1:1 or higher depending upon a particular purpose. In other embodiments, the ratio between the drive shaft gear 337 and the swing gear 348 is in the range of about 2:1. In still other embodiments, the ratio between the drive shaft 337 gear and the swing gear 348 is in the range of about 3:1. In yet other embodiments, the ratio between the drive shaft 337 gear and the swing gear 348 is in the range of about 3.88:1. In still other embodiments, the ratio between the drive shaft 337 gear and the swing gear 348 is in the range of about 4:1.

Turning now to FIGS. 10-14 which show the surgical device 300 disposed in the rotational mode allowing full 360° rotation of the drill bit 100 about the drill bit axis. Full rotation of the drill bit 100 may be particularly suited for plunge cutting while oscillation of the drill bit 100 may be better suited for finer tissue and bone shaving. Surgical device 300 enables the surgeon to switch easily between the two cutting modes (and with varying cutting or shaving aggressiveness) without having to substitute instruments or drill bits 100.

If the surgeon wishes to switch surgical device 300 from the oscillation mode to the rotational mode, the surgeon depresses lever lock 380 in a similar fashion as described above and further rotates the housing 320 relative to the collet 365 past aperture 382*a* (or in embodiments, in the opposite direction past aperture 382*a*) to a rotational mode locking position wherein a rotational locking aperture 382R mechanically engages the lever lock 380 therein. Simultaneously with the housing 320 being rotated past aperture 382*a*, the drive gear housing 390 is also toggled within housing 320 to a rotational mode position as denoted by the arrow "RM" of FIG. 10.

Figure 11:
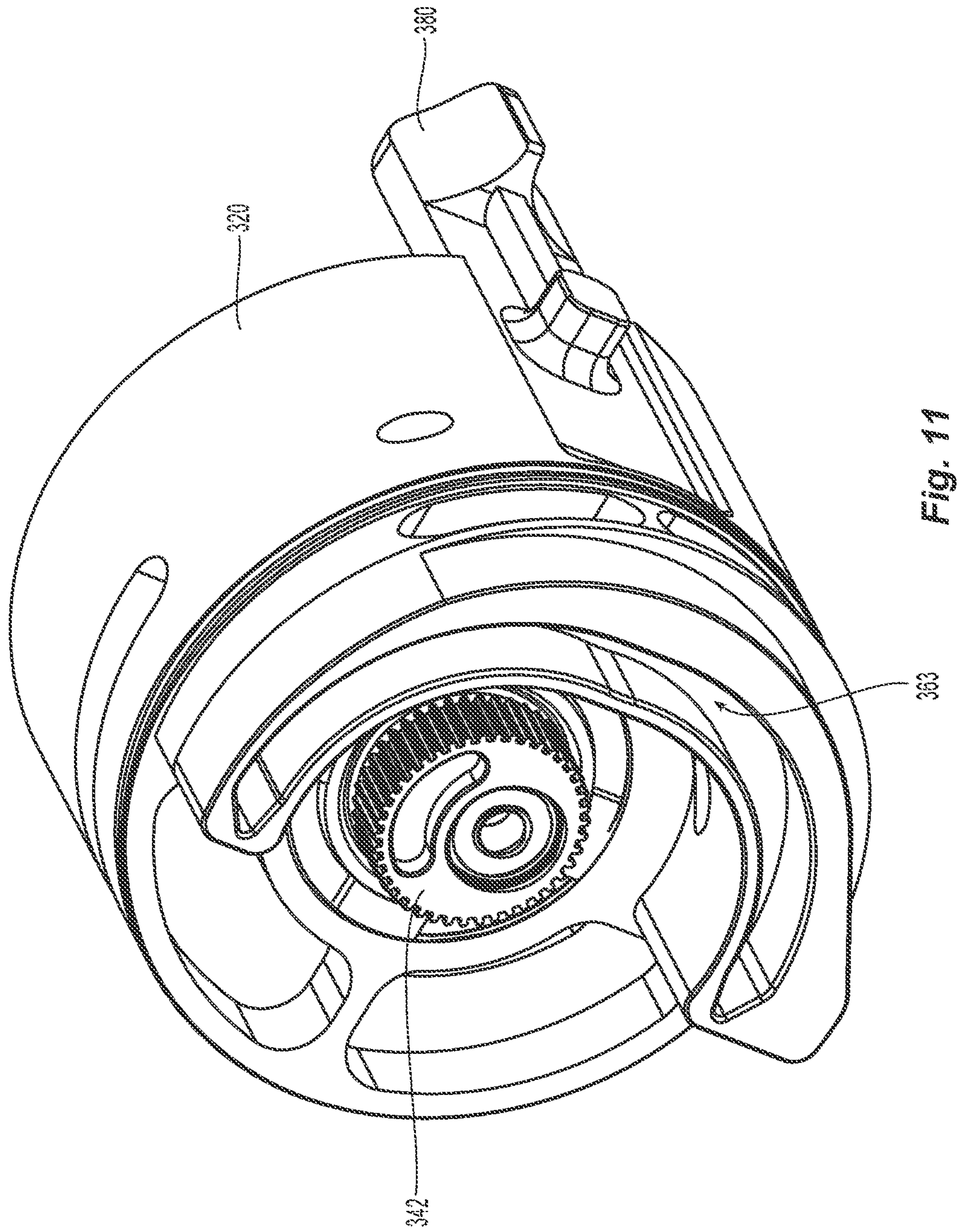
FIG. 11 is a perspective view of a gear housing for a drive assembly that cooperates with the drive gear housing to move the surgical device between the rotational mode and the oscillation mode upon rotation thereof.
Figure 12:
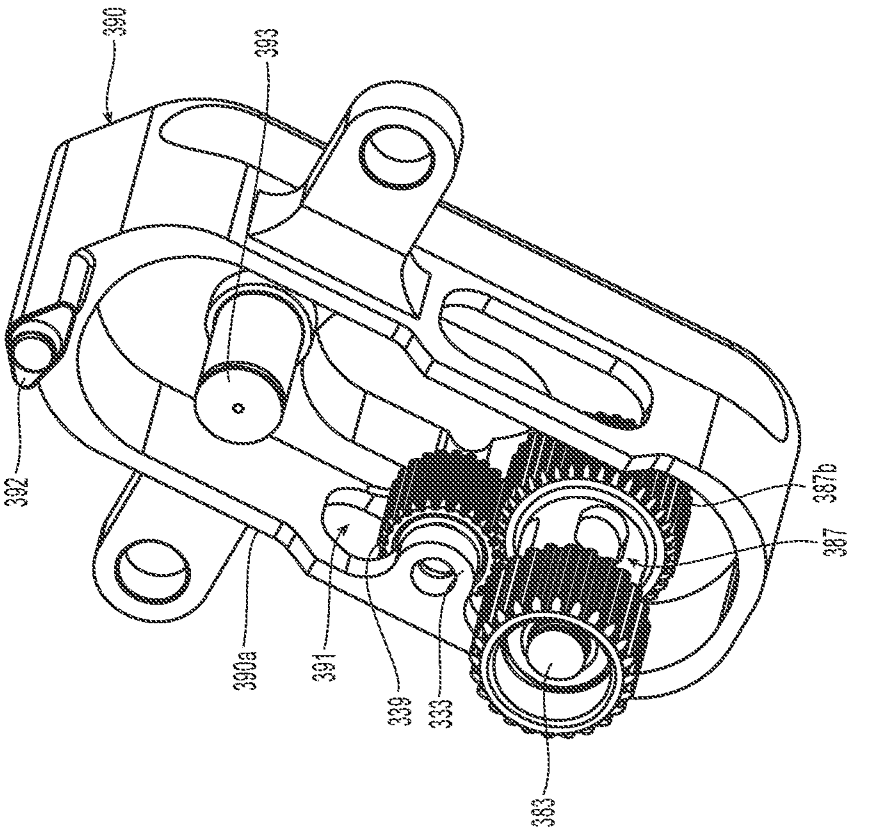
FIG. 12 is a perspective view of the drive gear housing of FIG. 10.
Figure 13:
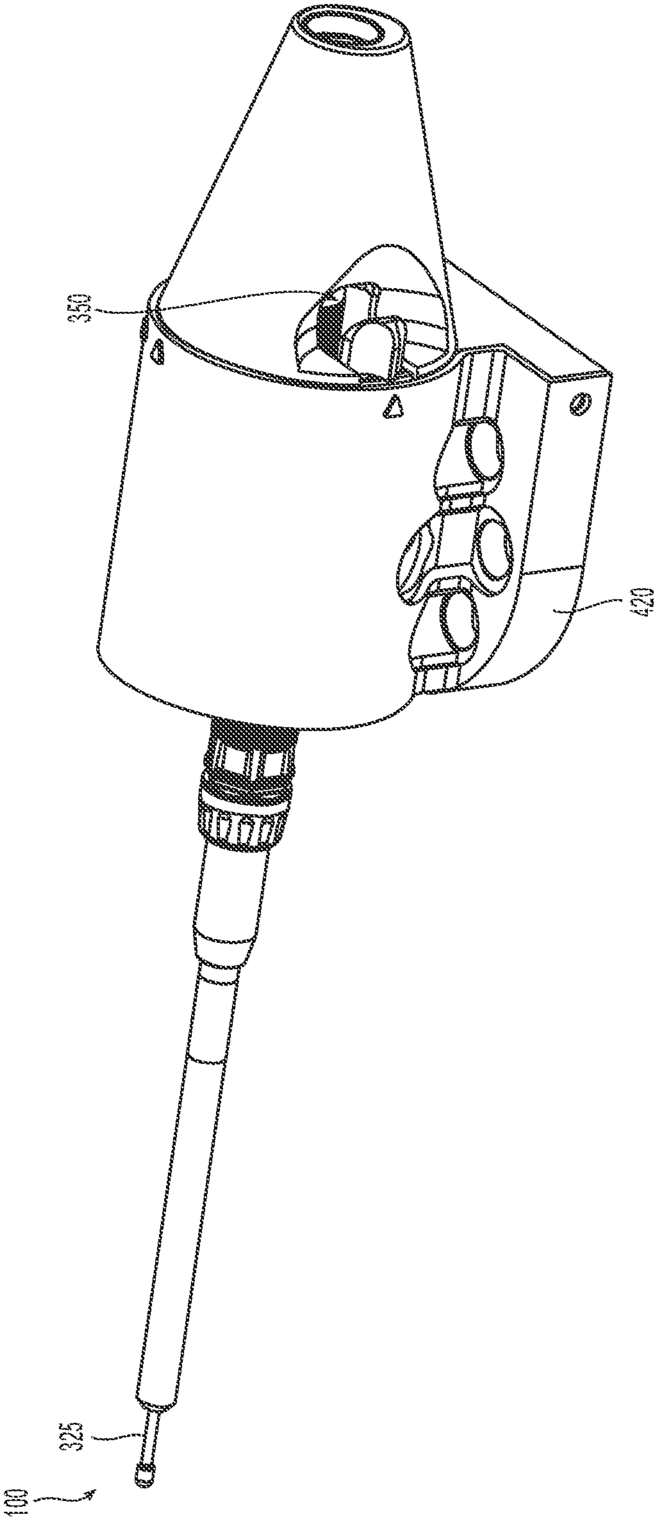
FIG. 13 is a rear, perspective view of the surgical device of FIGS. 6A-12 shown in a rotational mode.

More particularly and as best shown in FIG. 12, drive gear housing 390 includes an axle 393 that supports swing gear 348, an axle 333 that supports idle gear 339 and an axle 383 that supports direct drive gear 387. Drive gear housing 390 also includes a post 392 that is configured to ride within a corresponding guide slot 363 defined within a distal end of housing 320 (FIG. 11). A pin groove 391 is defined within a side 390*a* of the drive gear housing 390*a* and is configured to restrict the movement of the idle gear 339 to linear movement therein, e.g., "up" and "down" or "toggle-like". As the user rotates the lever lock 380 past aperture 382*a* and continues to rotate the housing 320, the post 392 rides along slot 363 causing the housing 320 to move along the path of the post 392, which, in turn, carries the various internal gears therealong with the movement of the drive gear housing 390, namely, swing gear 348, idle gear 339, and direct drive gear 387. The pin groove 391 restricts movement of the entire drive gear housing 390 as the post 392 rides within slot 363 until the movement of the post 392 and the orientation of the pin grove 391 generally align thereby allowing the drive gear housing 390 to move along with the internally gearing disposed therein. At this first point along the path of the post within the slot 363, the swing gear 348 disengages from the gear of the drive shaft 337 to take the oscillation mode offline. It is important to note that the link 344 remains connected to the gear output shaft 342 and moves the swing gear 348 but the swing gear 348 is no longer engaged with the gear of the drive shaft 337.

Figure 14:
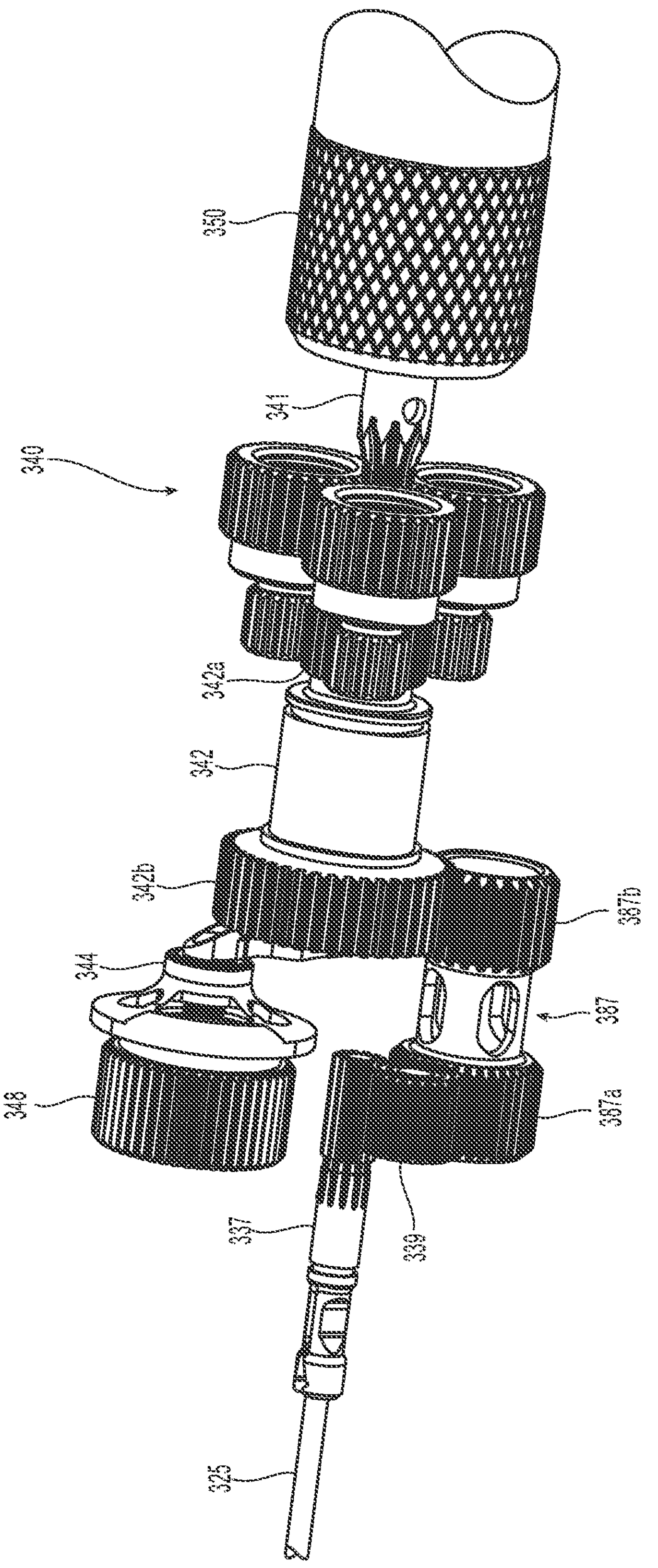
FIG. 14 is a rear, perspective view of the internal gear arrangement of the surgical device of FIGS. 6A-13 when disposed in the rotational mode.
Figure 15A:
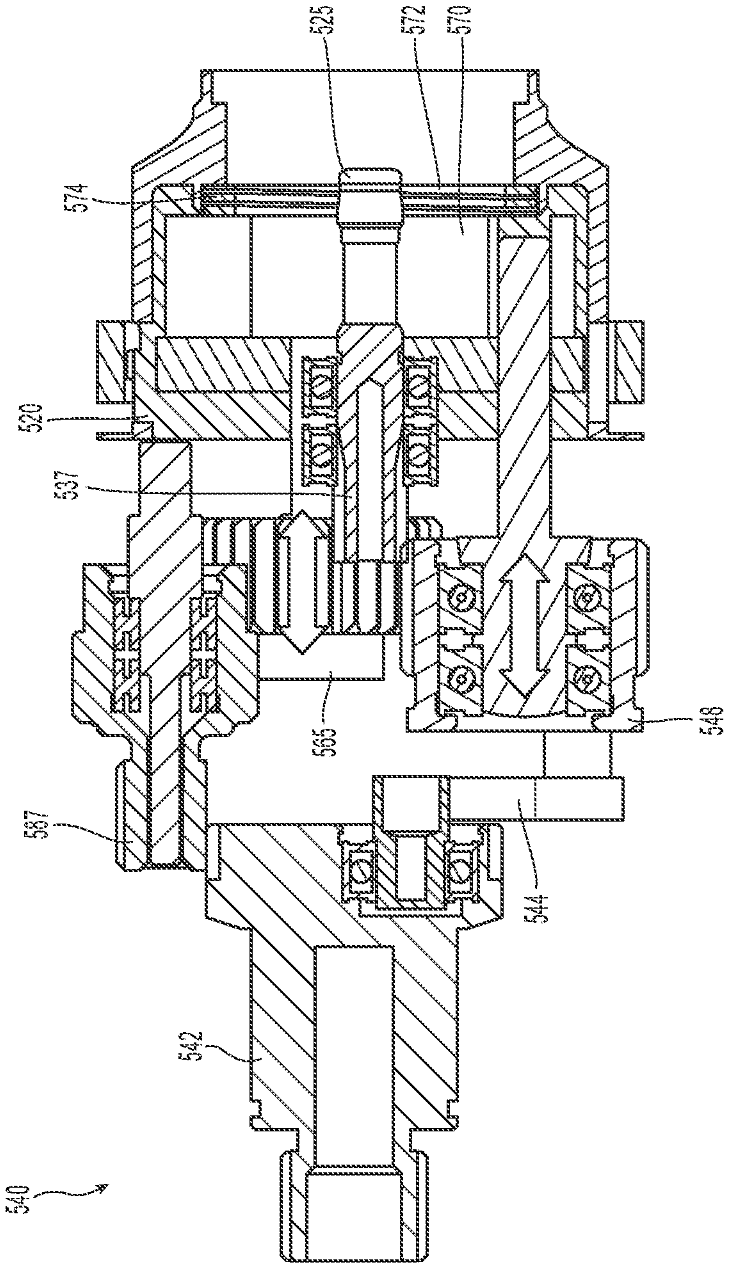
FIGS. 15A-15B are schematic representations of an alternate embodiment of a gear assembly for use with the shaving surgical device wherein the gear housing cooperates with the drive gear housing to move the surgical device between the rotational mode and the oscillation mode through movement of a common transmission gear.
Figure 15B:
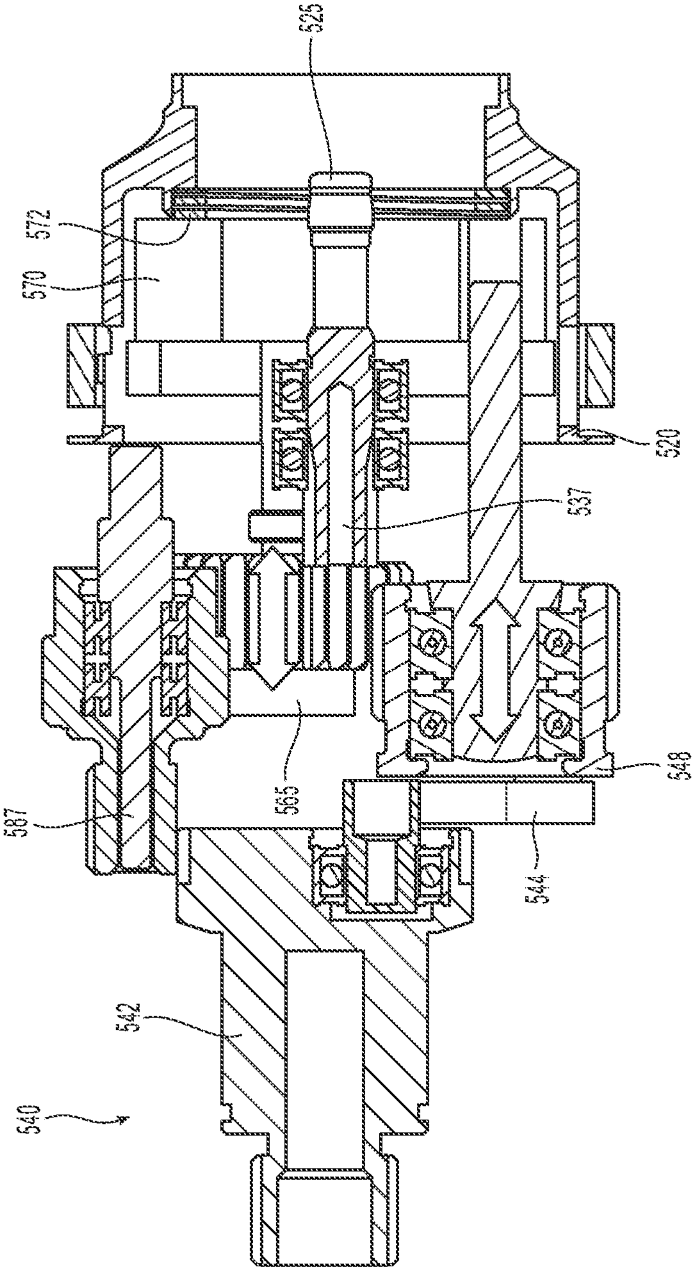
Figure 16A:
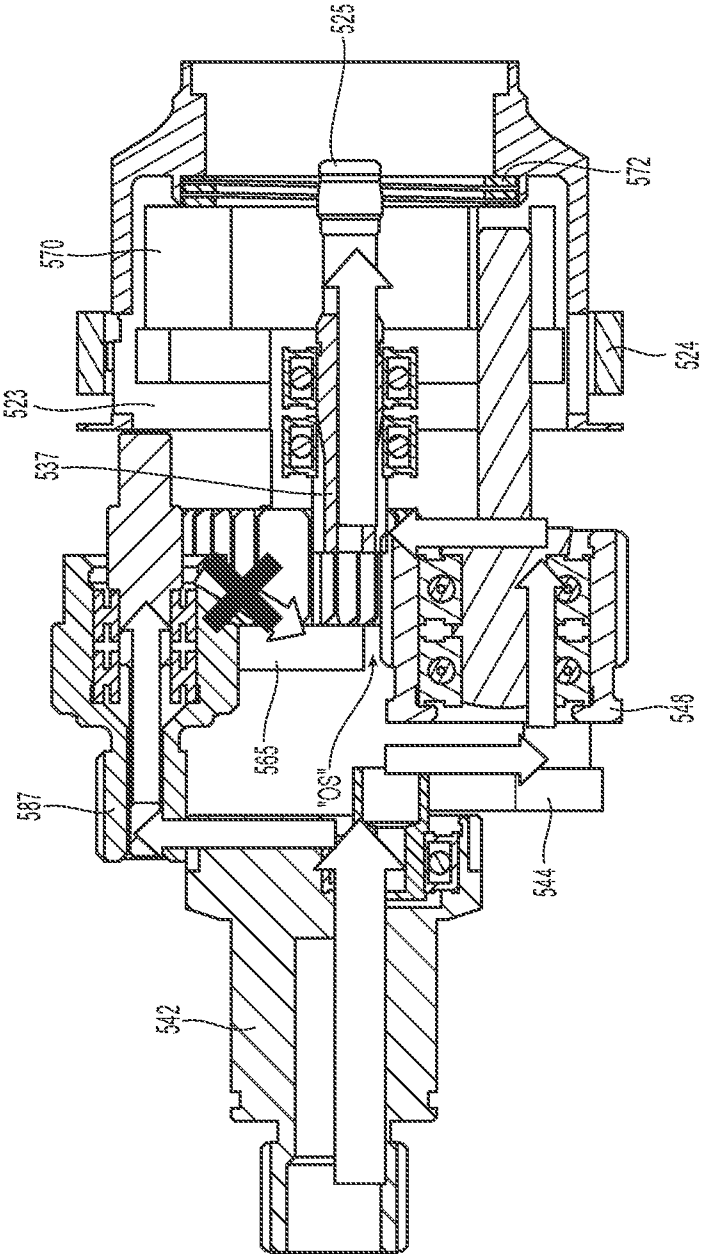
FIGS. 16A-16B are schematic representations of the embodiment shown in FIGS. 15A-15B showing the inter-engagement of the various gears and respective gear motion during the two different operational modes.
Figure 16B:
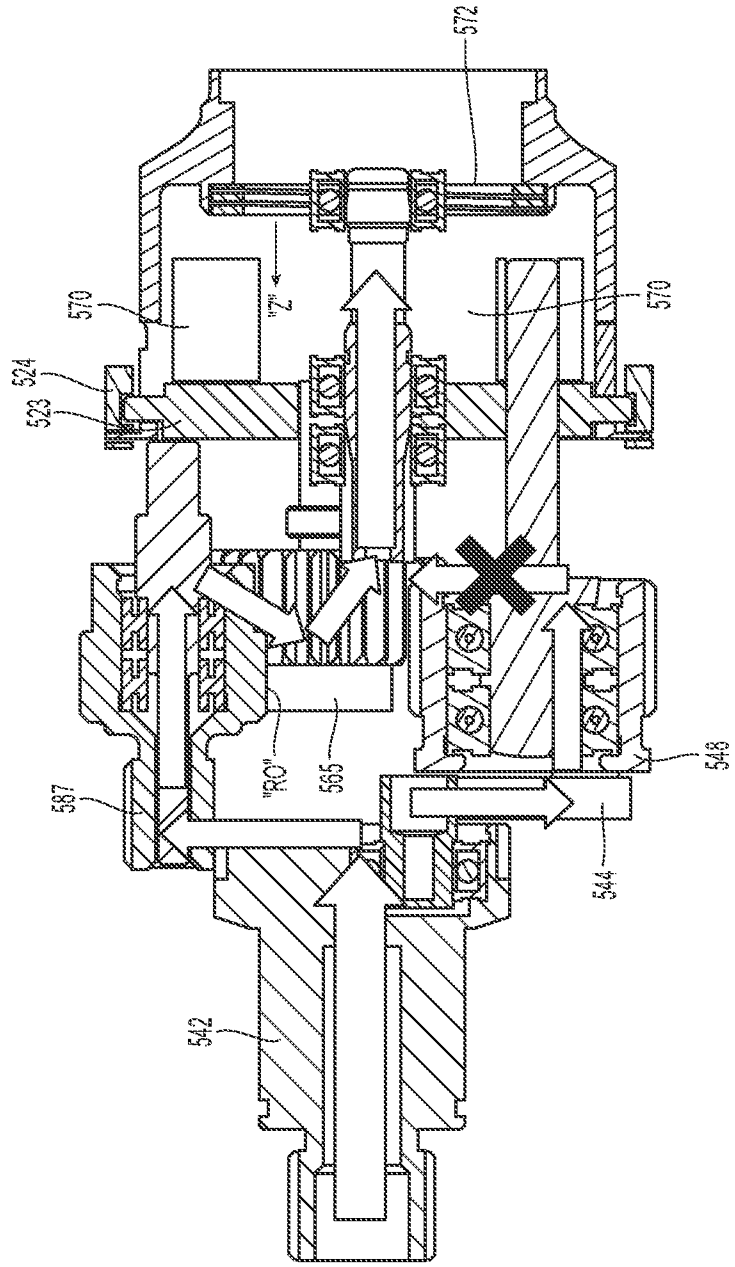

As the housing 320 is further rotated and the post 392 moves further along the slot 363, the idle gear 339 engages the gear of the drive shaft 337 while maintaining engagement with a distal end 387*a* of the direct drive gear 387 (FIG. 14). Moreover, as the post 392 moves within slot 363 and the idle gear 339 engages the gear of the drive shaft 337, the proximal end 387*b* of the direct drive gear 387 simultaneously engages a distal end 342*b* of the gear output shaft 342. The proximal end 342*a* of the gear output shaft 342 engages the gear assembly 340 which, in turn, connects to the motor 350 (FIG. 14). Once engaged, one or more pins 399 selectively lock the drive gear housing 390 in position. Surgical device 300 is now disposed in the rotational mode (FIG. 13) and surgeon can us the same drill bit 100 for cutting tissue or bone.

Turning back to FIGS. 6C and 6D, the exposure of the drill bit 100 may be controlled while keeping the tool shaft 325 in a locked orientation as described above. More particularly, a proximal end 314 of the elongated tube 312 may be coupled to housing 320 and positioned atop the tube 312 such that it is selectively rotatable thereabout via a tool exposure mechanism 330 (similar to tool exposure mechanism 30 described above). An inner periphery of the proximal end 314 includes a helical groove 314*a* defined therealong which is configured to receive a ball bearing 309 therein when the proximal end 314 is assembled atop tube 312. An outer periphery of tube 312 includes a pocket 311*a* that is configured to secure the ball bearing 309 therein such that it extends partially therefrom. When assembled, the ball bearing 309, pocket 311*a*, and helical groove 314*a* are aligned such that rotation of the proximal end 314 which is fixed to the housing 320 forces the ball bearing 309 along the helical groove 314*a* which, in turn, translates the tube 312 relative to the tool shaft 325 to vary the exposure of the drill bit 100.

For example, rotation of the proximal end 314 in the direction Rcw causes the ball bearing 309 to move distally along track 314*a* which, in turn, retracts the elongated tube 312 relative to the drill bit 100 for more tool exposure "E3" for surgical purposes (See Arrow "RET"—FIG. 6C). Rotation of the proximal end 314 in the direction Rccw causes the ball bearing 309 to move distally along groove 314*a* which, in turn, extends the elongated tube 312 relative to the drill bit 100 for less tool exposure "E4" for surgical purposes (See Arrow "EXT"— FIG. 6D).

Turning back to FIGS. 6E and 6F, an alternate embodiment of a locking collar 370 for selectively engaging the surgical tool 100 within the housing 320 is shown and includes a similar helical groove and bearing arrangement as described above with respect to the tool exposure mechanism 330. More particularly, locking collar 370 includes a helical groove 370*a* defined therein that extends therealong and that is configured to receive a ball bearing 372 at least partially therein. A collet 35 is seated within distal end of the housing 320 and includes a pocket 333*a* defined therein configured to receive the ball bearing 372 therein. Collet 335 includes a locking bearing disposed therein which is configured to operatively couple the distal end 337*a* of the drive shaft 337 with the proximal end 325*a* of the tool shaft 325 upon engagement thereof. The distal end 337*a* of the driveshaft 337 and the proximal end 325*a* of the tool shaft 325 may include mechanically mating features to facilitate initial engagement thereof, e.g., snap-fit members, keyed, push-fit, tongue and groove, screw-fit, and ball and socket, etc. and which can provide the surgeon with haptic feedback during loading and unloading of the tool shaft 325. In embodiments, the distal end 337*a* of the drive shaft 337 includes a plurality of fork-like tines 337*a*' that cooperate in a spring-like manner to facilitate engagement with the proximal end 325*a* of the tool shaft 325.

To load the tool shaft 325 into the surgical device 300, the locking collar 370 is rotated to a proximal-most position as shown in FIG. 6E. The tool shaft 325 is then inserted through elongated tube 312 (FIG. 7B) into engagement with the distal end 337*a* of the driveshaft 337 and pushed to fully seat the proximal end 325*a* therein. Once seated, the locking collar 370 is rotated in the direction "L" which moves helical ball 372 along the helical groove 370*a* which, in turn, forces the collet 335 distally. The distal end 337*a* of the drive shaft 337 remains stationary while the bearing 333 moves with the collet 335 over the distal end 337*a* of the drive shaft 337 which clamps onto the proximal end 325*a* of the tool shaft 325 to secure the tool shaft 325 within the collet 325. To release the tool shaft 325, the user simply rotates the locking collar 370 in the opposite direction and pulls the drill bit 100 and tool shaft 325 from the distal end 337*a* of the drive shaft 337. A new drill bit 100 and tool shaft 325 may be substituted.

Turning now to FIGS. 15A-16B which show an alternate embodiment of a gear assembly 540 for use with the surgical device 10 in accordance with the present disclosure that enables a user to switch between oscillation and rotary modes. For the purposes of brevity, only those aspects of gear assembly 540 are described in necessary detail to convey the operation of the gear assembly 540, however, it is contemplated that gear assembly 540 may be configured to work with any of the embodiments and/or components of FIGS. 1-14 described above.

More particularly, gear assembly 540 includes a motor output shaft 542 that is configured to operably couple to an oscillating link 544 (as described above with respect to FIGS. 4A-4C) and a direct drive gear 587 (as described above with respect to FIG. 14). Link 544, in turn, connects to a swing gear 548 at an opposite end thereof which is configured to move in and out of engagement with a transmission gear 565 common to drive gear 587. Drive gear 587 is also configured to move in and out of engagement with transmission gear 565.

Transmission gear 565 is disposed within housing 520 and is moveably coupled with a support chassis 570 such that, when actuated, the transmission gear 565 engages either the swing gear 548 to oscillate shaft 525 (as described in detail above with respect to FIGS. 1-14) or the drive gear 587 to fully rotate shaft 525 (as also described above). The transmission gear 565 also meshingly engages the proximal end 537 of the tool shaft 525. A guide plate 523 may be configured to align the shafts of the respective gears 548, 565 and 587 within the housing 520 and guide the support chassis 570 during transition between modes and may be configured to rotate (or otherwise move) into a locked position to secure the gear assembly 540 into a chosen mode of operation, e.g., oscillatory or rotary motion of shaft 525. An outer ring 524 may be configured to lock the guide plate 523 in the respective oscillation or rotary mode upon rotation, lateral movement, and/or longitudinal movement thereof relative to the guide plate 523.

In order to transition between modes, the user moves the outer ring 524 relative to the housing 520 (via rotation or other movement) which moves the support chassis 570 with the assistance of a spring 572 and positions the swing gear 548 in engagement with the transmission gear 565 or the direct drive gear 587 in engagement with the transmission gear 565. Once in a desired mode of operation, the user can lock either gear (gear 548 or gear 587) in engagement prior to activation.

Figure 17:
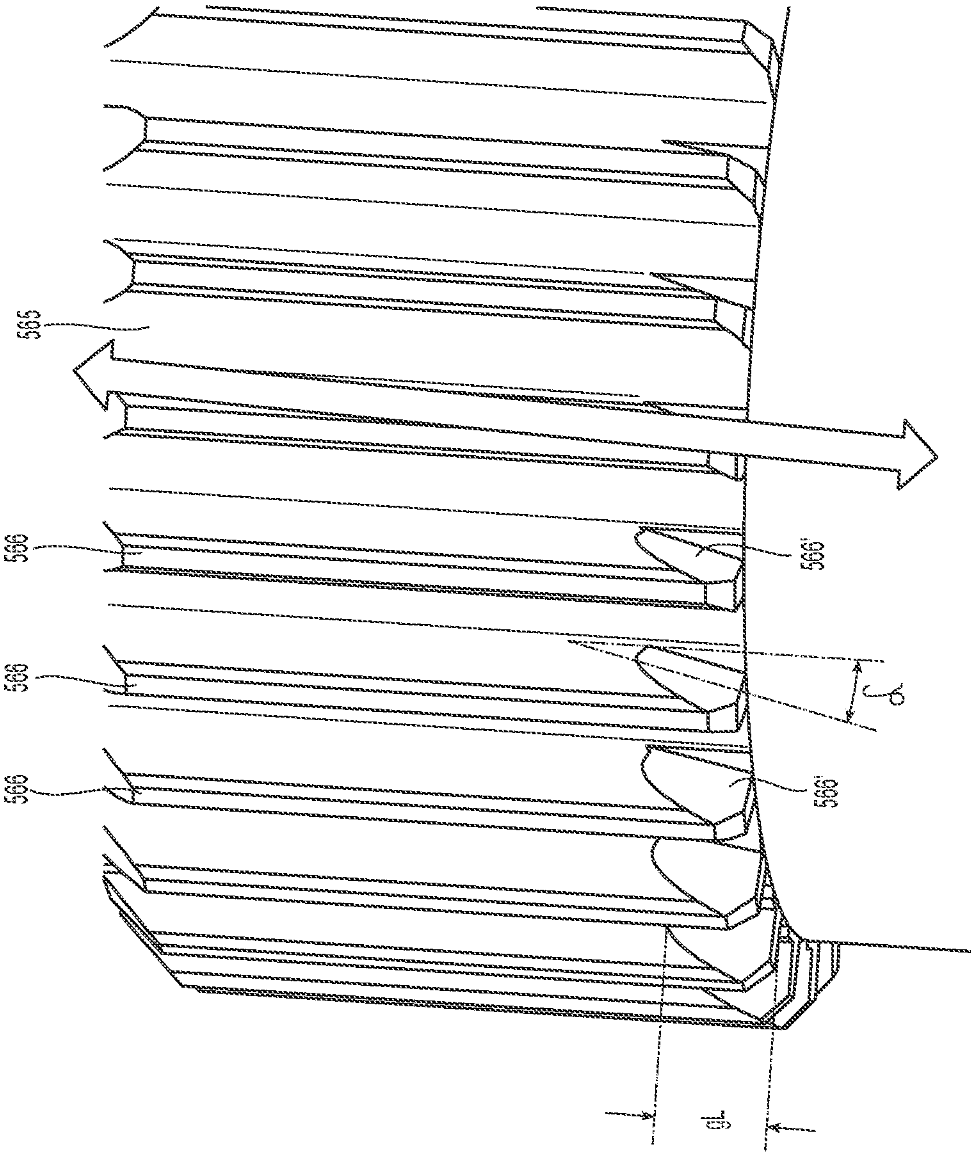
FIG. 17 is an enlarged perspective view of one of the gears showing a chamfered profile of the respective gear teeth to facilitate meshing between gears especially if slightly misaligned when switching between operational modes.
Figure 18A:
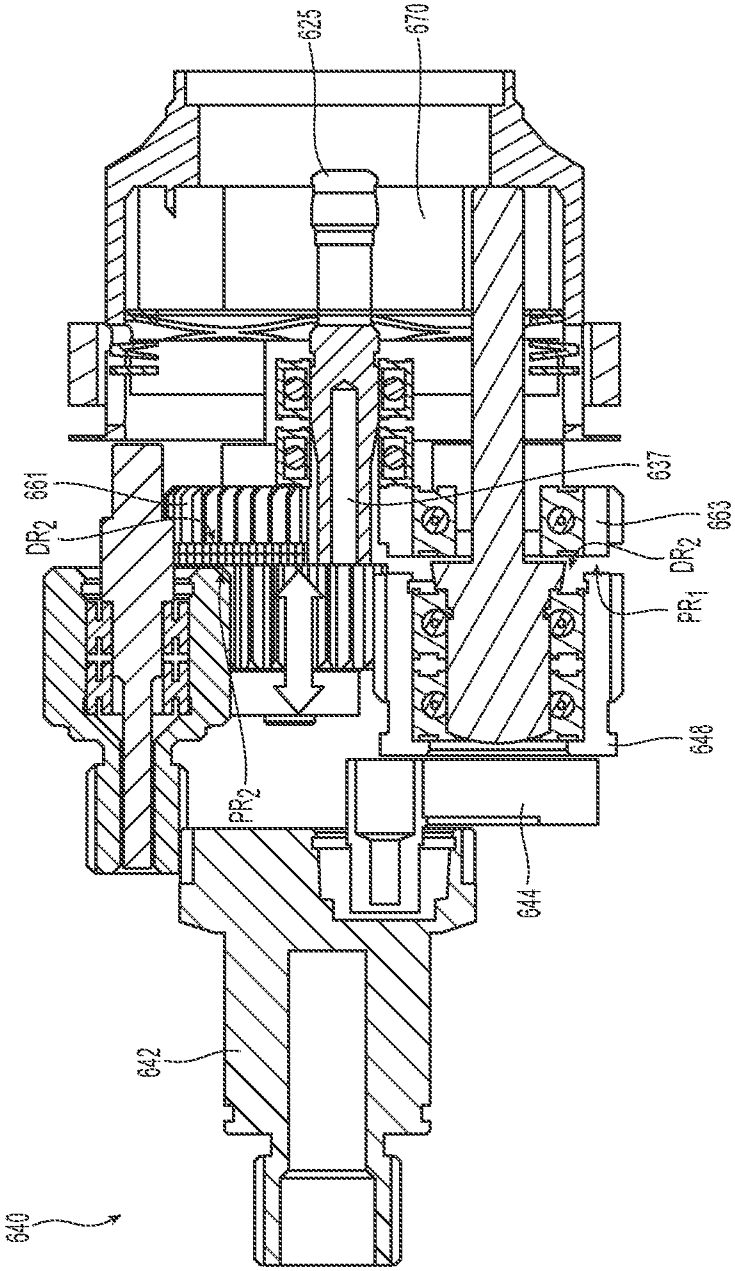
FIGS. 18A-18B are schematic representations of another alternate embodiment of a gear assembly for use with the shaving surgical device wherein the gear housing cooperates with the drive gear housing to move the surgical device between the rotational mode and the oscillation mode through engagement with a toggle gear.
Figure 18B:
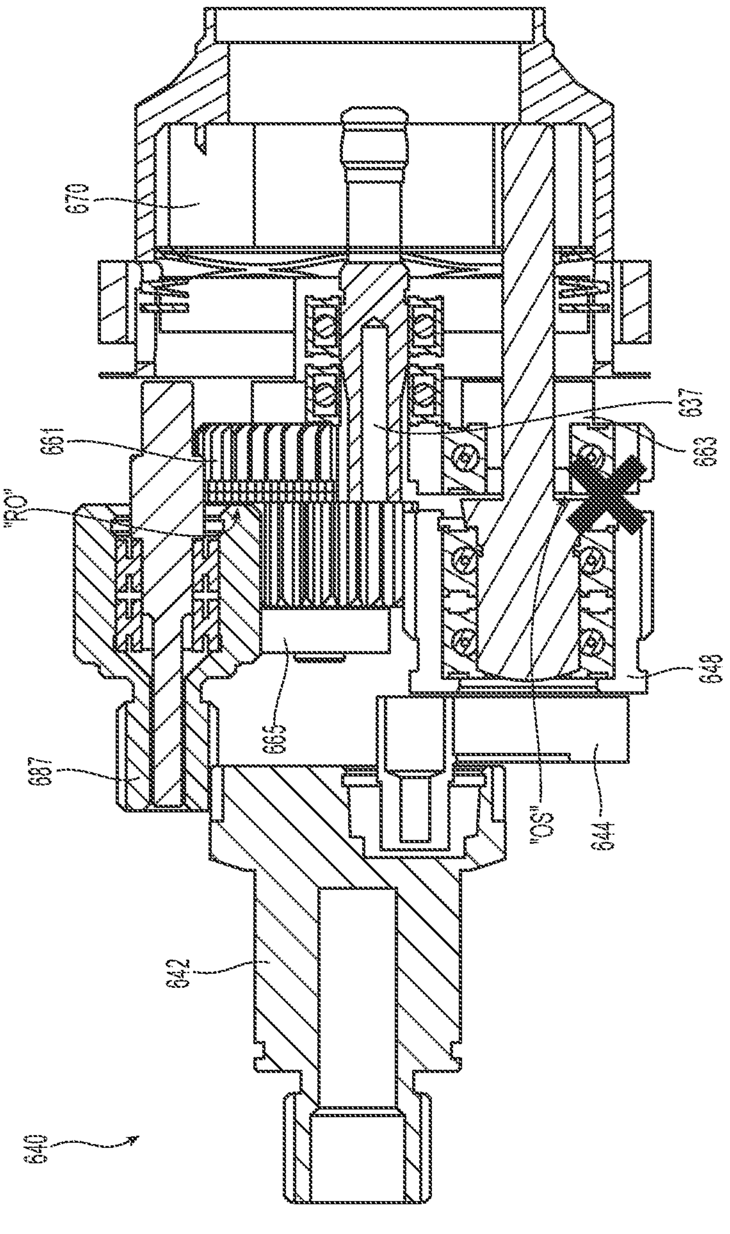
Figure 19A:
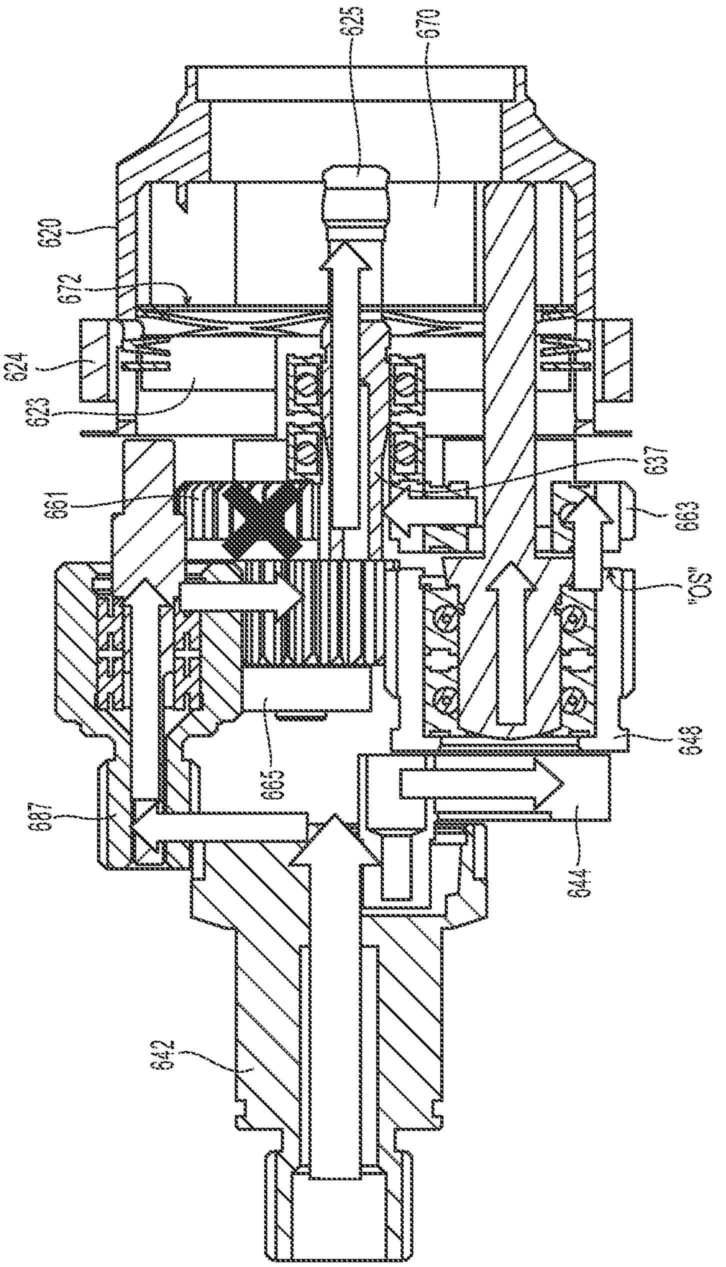
FIGS. 19A-19B are schematic representations of the embodiment shown in FIGS. 18A-18B showing the inter-engagement of the various gears and respective gear motion during the two different operational modes.
Figure 19B:
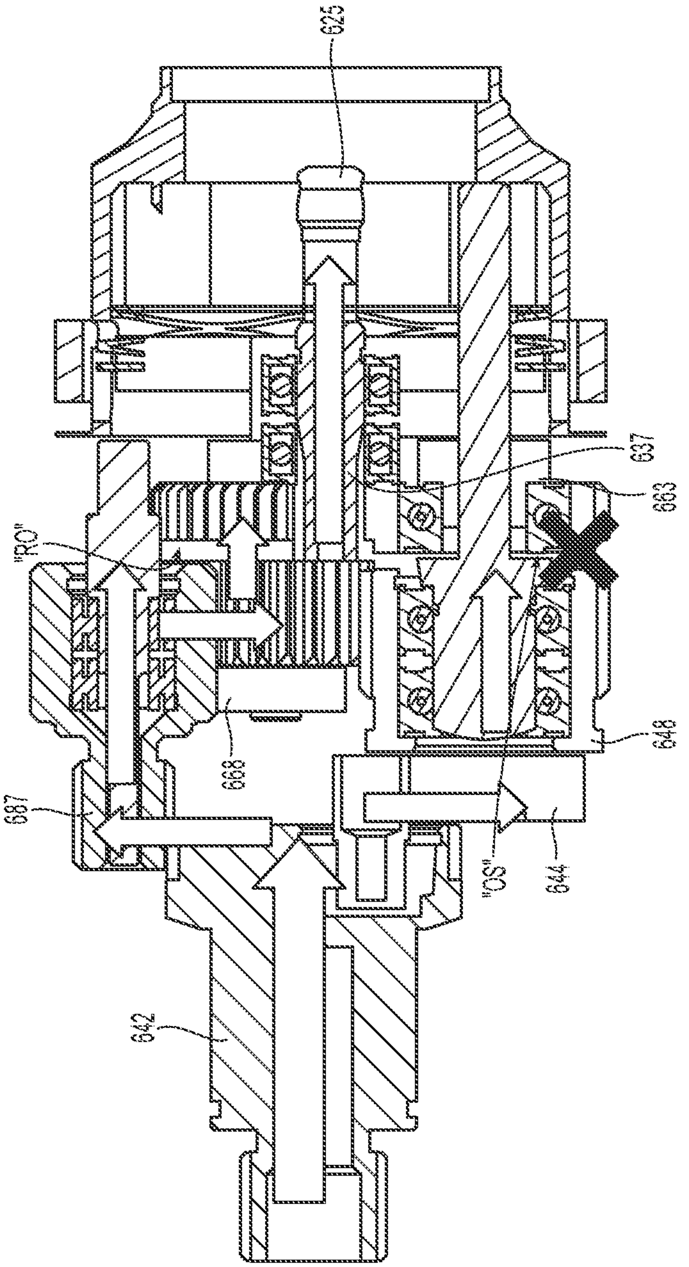

During transition between modes, one or more gears, e.g., transmission gear 565 and one end of drive gear 587, may not fully align prior to engagement thereof. In order to facilitate engagement and proper meshing between respective gear teeth, e.g., transmission gear 565 and/or drive gear 587, one or both gears may include a chamfered surface 566' defined on one side of the respective gear teeth 566 thereof (FIG. 17). Chamfered surface 566' may be cut, polished, honed, grinded or otherwise formed in each gear tooth 566 in any known fashion in the art. It is contemplated that cutting the chamfered surface 566' at a smaller angle £ may be more beneficial for lowering the insertion force between the gear teeth of the transmission gear 565 and the drive gear 587. Moreover, reducing the overall surface area of one or both of the inter-engaging surfaces between the transmission gear 565 and the drive gear 587 may also facilitate gear synchronization between modes. For example, the bottom surface area of the chamfered surface 566' (FIG. 17) of transmission gear 565 and the corresponding top surface area of the chamfered surface (not shown) of drive gear 587 may be honed to a sharp edge to facilitate gear synchronization.

The chamfered surface 566' may extend along each gear tooth 566 a length "gl" and be cut at an angle £ which may range from about 5 degrees to about 35 degrees depending upon a particular purpose. This may also facilitate gear synchronization between modes. In other embodiments, the angle £ may range from about 20 degrees to about 35 degrees depending upon a particular purpose to facilitate gear synchronization. In embodiments, the angle £ may range from about 5 degrees to about 20 degrees depending upon a particular purpose to facilitate gear synchronization. Either one or both the transmission gear 565 and the drive gear 587 may include chamfered surfaces 566' that facilitate gear synchronization either independently or in combination.

Turning now to FIGS. 18A-19B which show another embodiment of a gear assembly 640 for use with the surgical device 10 in accordance with the present disclosure that enables a user to switch between oscillation and rotary modes. For the purposes of brevity, only those aspects gear assembly 640 are described in necessary detail to convey the operation of the gear assembly 640, however, it is contemplated that gear assembly 640 may be configured to work with any of the embodiments and/or components of FIGS. 1-14 described above.

More particularly, gear assembly 640 includes a motor output shaft 642 that is configured to operably couple to an oscillating link 644 (as described above with respect to FIGS. 4A-4C) and a direct drive gear 687 (as described above with respect to FIG. 14). Link 644, in turn, connects to a swing gear 648 at an opposite end thereof which is configured to move in and out of engagement with a synchronization gear 663 which, in turn, engages transmission gear 665. Drive gear 687 is configured to move in and out of engagement with a second synchronization gear 661 which, in turn, commonly engages transmission gear 665.

Synchronization gears 661 and 663 include proximally-facing blocker rings PR2, PR1 that are configured to mesh with respective distally-facing blocker rings DR2, DR1 disposed on drive gear 687 and swing gear 648 when moved into engagement therewith. Transmission gear 665 is disposed within housing 620 and is supported on chassis 670. The guide plate 623 supports synchronization gears 661 and 663 in a toggle-like manner atop a spring 672 such that, when actuated, only one gear, e.g., either gear 661 or gear 663, engages the transmission gear 665 to control the movement of the shaft 625.

In embodiments, the blocker rings PR2, PR1 of the synchronization gears 661 and 663 are configured to engage both the respective counterpart gears, namely, swing gear 648 for gear 663 and drive gear 687 for gear 661, and a corresponding distally facing blocker ring associated with transmission gear 665 upon active engagement therewith to transfer respective movement to the shaft 625. In other embodiments, the blocker rings PR2, PR1 of the synchronization gears 661 and 663 are configured to engage both the respective counterpart gears, namely, swing gear 648 for gear 663 and drive gear 687 for gear 661, and the transmission gear 665 includes a compound gear (not shown) associated with transmission gear 665 that engages upon active engagement of the respective synchronization gear 661, 663 to transfer respective movement to the shaft 625. In other embodiments, one of the synchronization gears, e.g., gear 663, may be configured to engage the proximal end 637 of the shaft 625 upon engagement with the transmission gear 665.

The transmission gear 665 also meshingly engages the proximal end 637 of the tool shaft 625. The guide plate 623 may be configured to align the shafts of the respective gears 648, 665 and 687 within the housing 620. Outer ring 624 may be configured to lock the guide plate 623 in the respective oscillation or rotary mode upon rotation, lateral, and/or longitudinal movement thereof relative to the guide plate 623.

In order to transition between modes, the user moves the outer ring 624 relative to the housing 620 (via rotation or other movement) which moves the guide plate 623 with the assistance of the spring 672 and toggles the transmission gear 665 in engagement with one of the synchronization gears 661, 663 which actuates, respectively, the direct rotary drive gear 687 or the oscillatory swing gear 648. Once in a desired mode of operation, the user can lock the gears (drive gear 687 or the oscillatory swing gear 648) in engagement prior to activation.

Turning now to FIGS. 20A-24 which show alternate embodiments of oscillation mechanisms in accordance with the present disclosure which may be utilized with any of the aforementioned gear assemblies described above to oscillate the shaft of the surgical tool 100. More particularly, FIGS.

Figure 20B:
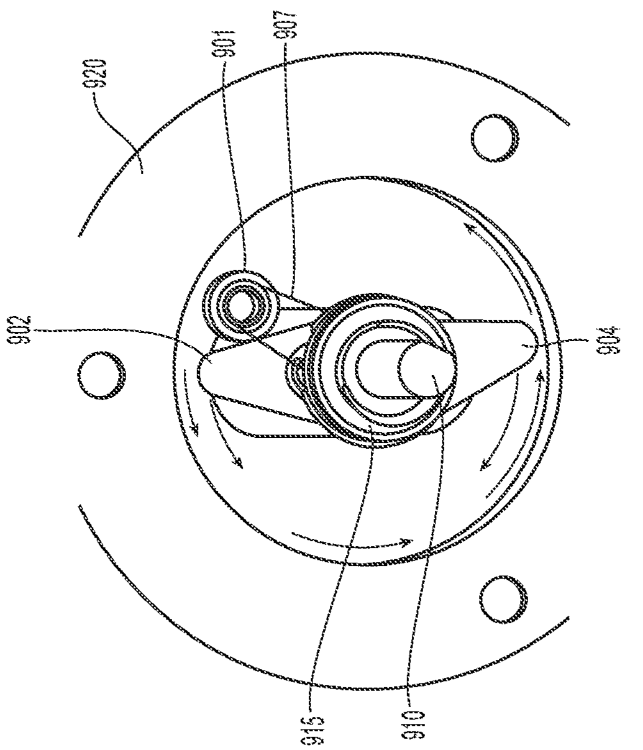
FIGS. 20A-20F are schematic representations of an alternate oscillation mechanism for use with the shaving surgical device including alternating oscillating paddles.
Figure 20A:
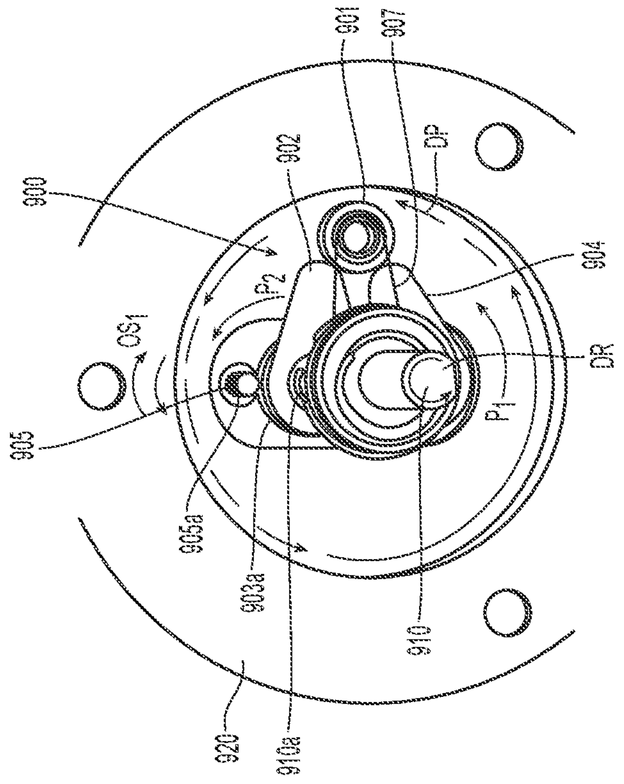
Figure 20D:
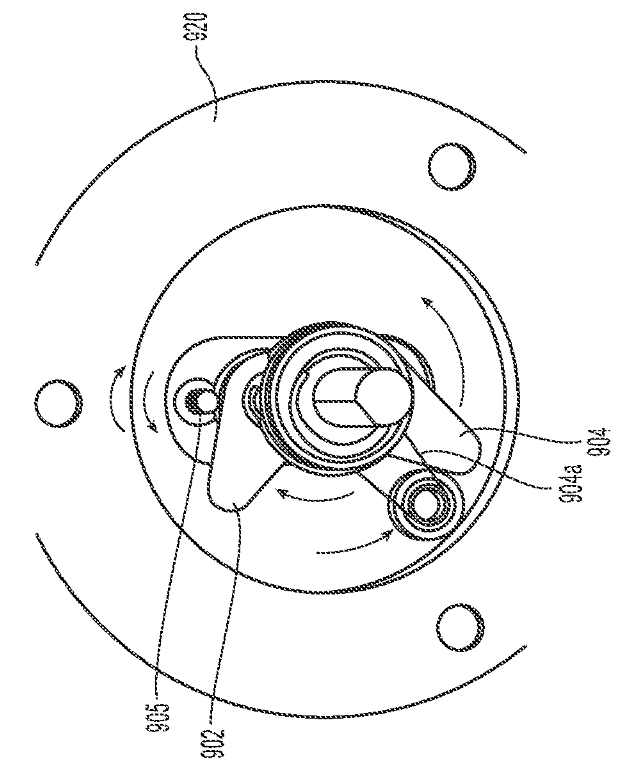
Figure 20C:
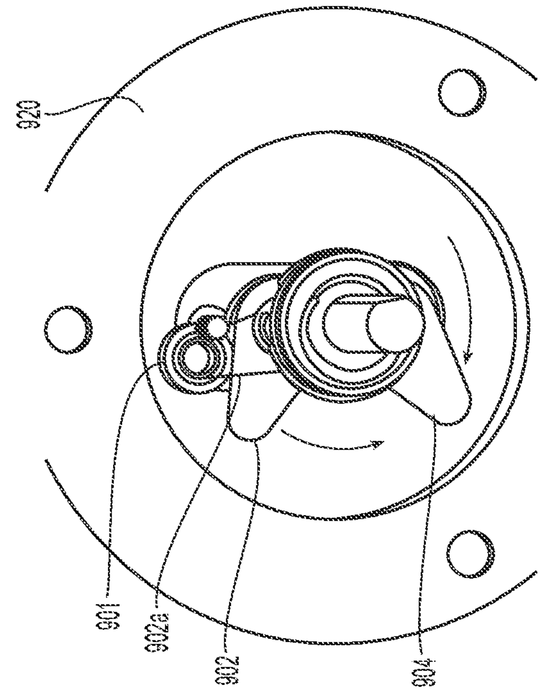
Figure 20F:
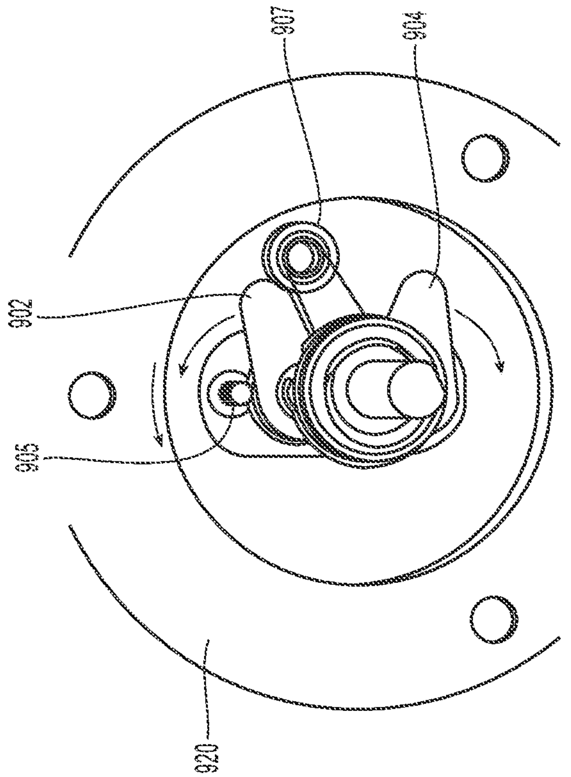
Figure 20E:
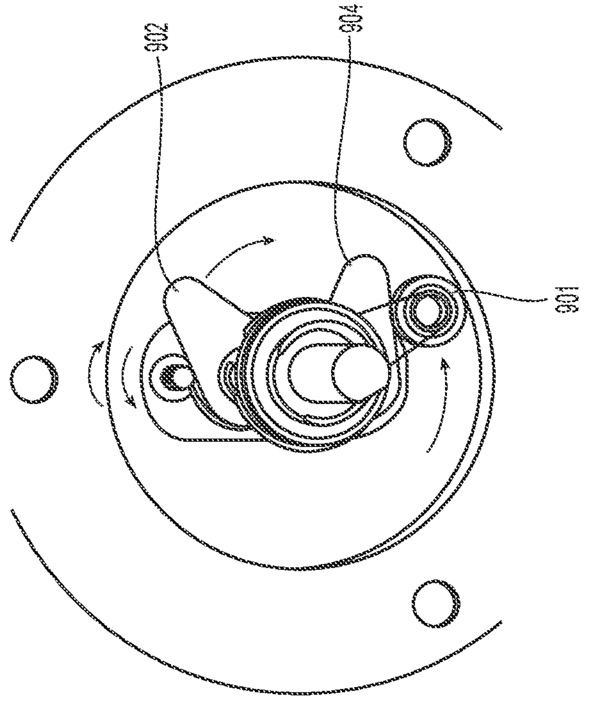

20A-20F show a gear driven oscillation mechanism 900 according to one embodiment in accordance with the present disclosure which includes a pair of opposing paddles 902 and 904 mounted on either side of a drive paddle 907 atop a drive rod 910 all housed within a gear housing 920. Drive paddle 907 rotates 360° in the direction of arrow "DP" of drive rod 910 which rotates 360° in direction of arrow "DR" (FIG. 20A). Opposing paddles 902 and 904 are secured atop a common drive rod shaft 910*a* at diametrically opposite ends thereof and rotate in opposite directions towards one another but not interfere with one another on either side of paddle 907.

As drive paddle 907 rotates each 360° revolution, drive paddle 907 will contact each respective paddle 902, 904 along the circumferential path. For example, as drive paddle 907 rotates drive paddle 907 will initially contact paddle 902 on an interfering edge 902*a* and force both paddles 902 and 904 to move with the drive paddle 907 in a first direction until the paddle 907 contacts the opposite paddle, e.g., paddle 904, on an interfering edge 904*a* thereof, and force both paddles 902 and 904 to move with the drive paddle 907 in an opposite direction. This process repeats causing the oscillating motion of the drive rod shaft 910*a* in the direction of arrow "OS1" (See FIGS. 20B-20F).

An opposite side of paddle 902 defines a rack 903*a* that is configured to engage a pinion 905*a* disposed on the oscillating shaft of the surgical tool 100. The oscillation of the drive rod shaft 910*a* is conveyed to the surgical tool 100 upon engagement of the drive shaft 910*a* to the pinion 905*a*. In embodiments, the geometry of the paddles 902, 904 and/or 907 may be manipulated to alter the degree or angle of oscillation of the surgical tool 100 depending upon a particular purpose.

Figure 21:
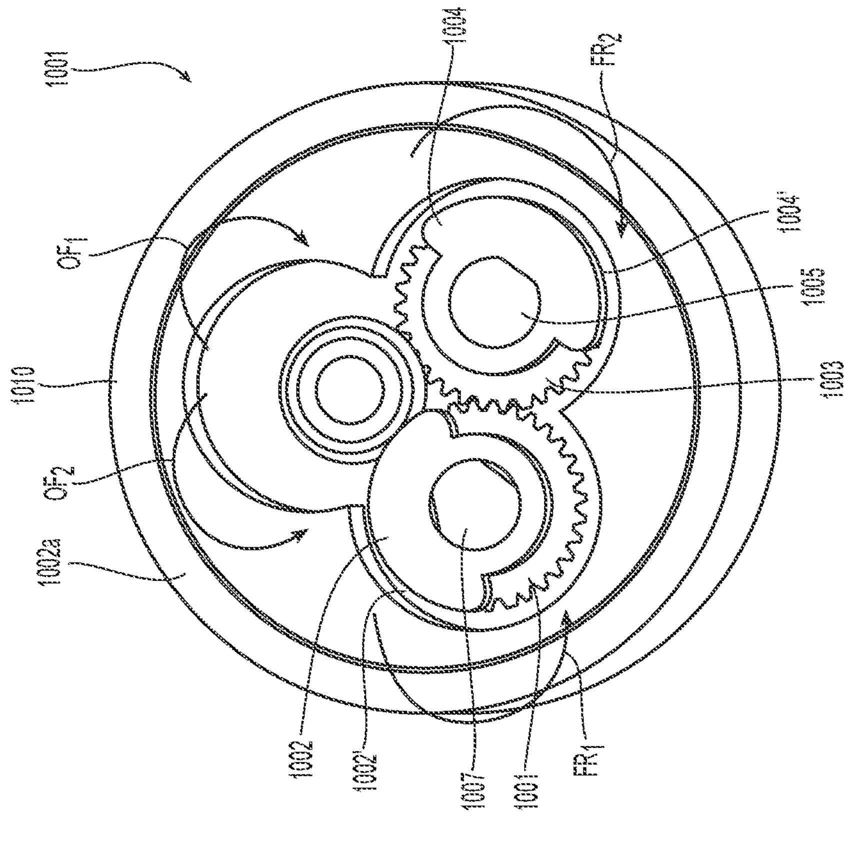
FIG. 21 is a schematic illustration of another alternate oscillation mechanism for use with the shaving surgical device including alternating friction discs.

Turning to FIG. 21 which shows another embodiment of a gear-like oscillation mechanism 1000 in accordance with the present disclosure. Oscillation mechanism 1000 includes a housing 1020 that is configured to support multiple shafts and gear assemblies arranged in parallel fashion that extend from the proximal motor input to the gear assembly output for oscillating the surgical tool 100. More particularly, shaft 1007 supports the input from the motor and drives rotation of a first gear 1001 in a first direction FR1. First gear 1001 meshes with a second gear 1003 that is mounted atop shaft 1005 and is configured to drive second gear 1003 in an opposite direction FR2. Each gear 1001, 1003 includes a respective friction disc 1002, 1004 that is mechanically engaged to the respective shafts 1007, 1005 of each gear 1001, 1003. The friction discs 1002, 1004 include arcuate surfaces 1002', 1004' that extend beyond the outer periphery of their respective gears 1001, 1003 enabling each arcuate surface 1002', 1004' to frictionally engage an outer surface of tool shaft 1010 during rotation thereof. The arcuate surfaces 1002', 1004' are keyed atop opposite sides of each respective shaft 1007, 1005 such that the respective arcuate surfaces 1002', 1004' do not contact one another during rotation, but, rather, narrowly miss one another during cooperative rotation therebetween allowing each to alternate frictional engagement with the tool shaft 1010. By alternating frictional engagement between the two frictional discs 1002, 1004 rotating in opposite directions, the shaft 1010 is forced to oscillate repeatedly as the friction discs 1002, 1004 continue to rotate.

For example, when shaft 1007 is rotated via input from the motor, both gears 1001, 1003 rotate which correspondingly rotate the frictions discs 1002, 1004. Friction disc 1002 rotates in the direction FR1 which contacts shaft 1010 at point 1002*a* to correspondingly rotate the shaft 1010 in the direction OF1. As the friction disc 1002 rotates beyond the trailing edge of the arcuate surface 1002' in engagement with shaft 1010, a leading edge of the arcuate surface 1004' of friction disc 1004 is timed to come into engagement with shaft 1010 and reverse rotation such that the shaft 1010 now rotates in the direction OF2. Similarly, as friction disc 1004 rotates beyond the trailing edge of the arcuate surface 1004' in engagement with shaft 1010, a leading edge of the arcuate surface 1002' of friction disc 1002 is timed to come into engagement with shaft 1010 and reverse rotation such that the shaft 1010 again rotates in the direction OF1. This process repeats causing the oscillating motion of the tool shaft 1010.

Figure 22:
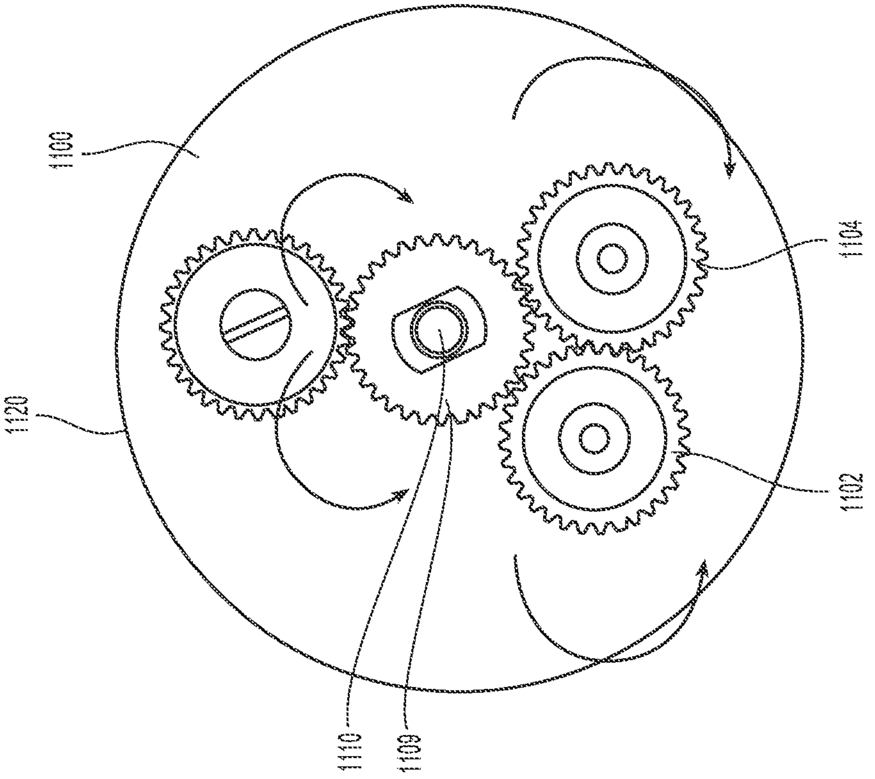
FIG. 22 is a schematic illustration of another alternate oscillation mechanism for use with the shaving surgical device including alternating compound gears.

Turning to FIG. 22 which shows yet another embodiment of a gear-like oscillation mechanism 1100 in accordance with the present disclosure. Oscillation mechanism 1100 includes a housing 1120 that is configured to support multiple shafts and gear assemblies arranged in parallel fashion that extend from the proximal motor input to the gear assembly output to the oscillating surgical tool 100. Generally speaking, oscillation mechanism 1100 operates in a similar fashion to oscillation mechanism 1000 with the exception that oscillation mechanism utilizes a pair of partial compound gears 1102, 1104 that are configured to engage a common gear 1109 disposed on shaft 1110 of the surgical tool 100. Initial input from the motor rotates gear 1102 in the first direction which, in turn, rotates the gear 1109 and shaft 1110 in the same direction until the partial compound geometry of gear 1102 disengages gear 1109 from gear 1102 and engages gear 1104 during the range of motion thereby reversing the direction of gear 1109 and shaft 1110. Gear 1102 and the motor input remain rotating in the same direction. As the gear 1104 continues to rotate gear 1109 and shaft 1110 in the same direction, the partial compound geometry of gear 1104 disengages gear 1109 from gear 1104 and engages gear 1102 during the range of motion again reversing the direction of gear 1109 and shaft 1110. Gear 1102 remains rotating in the same direction. This process repeats causing the oscillating motion of the tool shaft 1010.

Figure 23:
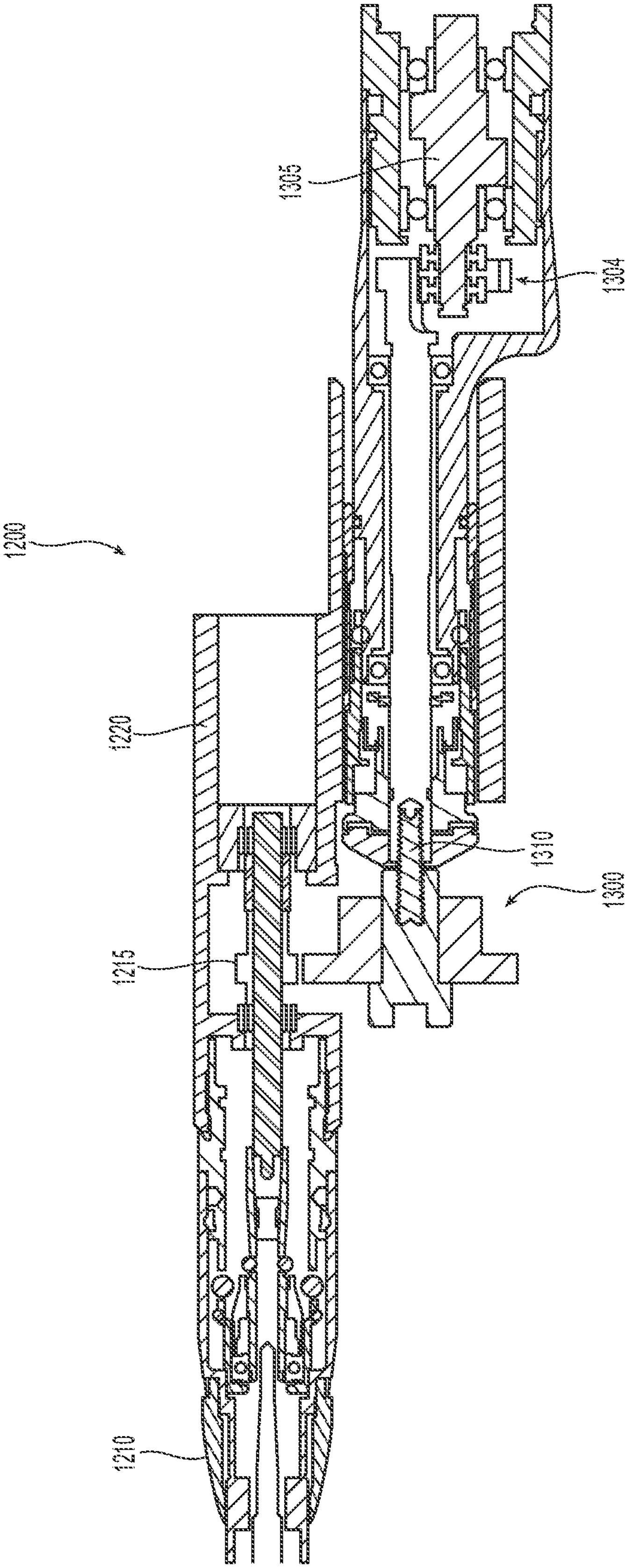
FIG. 23 is a schematic illustration of another alternate oscillation mechanism for use with the shaving surgical device including a gear oscillation boost mechanism that can boost the oscillation angle of an oscillating shaft.

In embodiments, one or more of the above-identified oscillation mechanisms may be utilized with an oscillation enhancement mechanism or an oscillation "boost" mechanism that is configured to increase the oscillation angle of the surgical tool 100 (See FIG. 23). More particularly, input from a motor shaft 1305 may be fed into any one of the aforementioned oscillation mechanisms described above, e.g., oscillation mechanism 1304, to produce an initial oscillation angle (For the purposes herein, in the range of about 5° outputted to tool shaft 1310). An oscillation enhancement tool 1300 may be operably engaged to the tool shaft 1310 and configured to boost the oscillation angle of the tool to an oscillation angle in the range of about 50° to about 90°. Any of the above-mentioned gear assemblies and oscillation mechanisms may be utilized to accomplish this purpose by simply utilizing the motor input of the tool shaft as the motor input described above. The enhancement tool 1300 may be operably coupled to one or more gears 1215 (or a gear assembly) disposed within a housing 1220 of an instrument 1200 and outputted to the surgical tool 1210.

Figure 24:
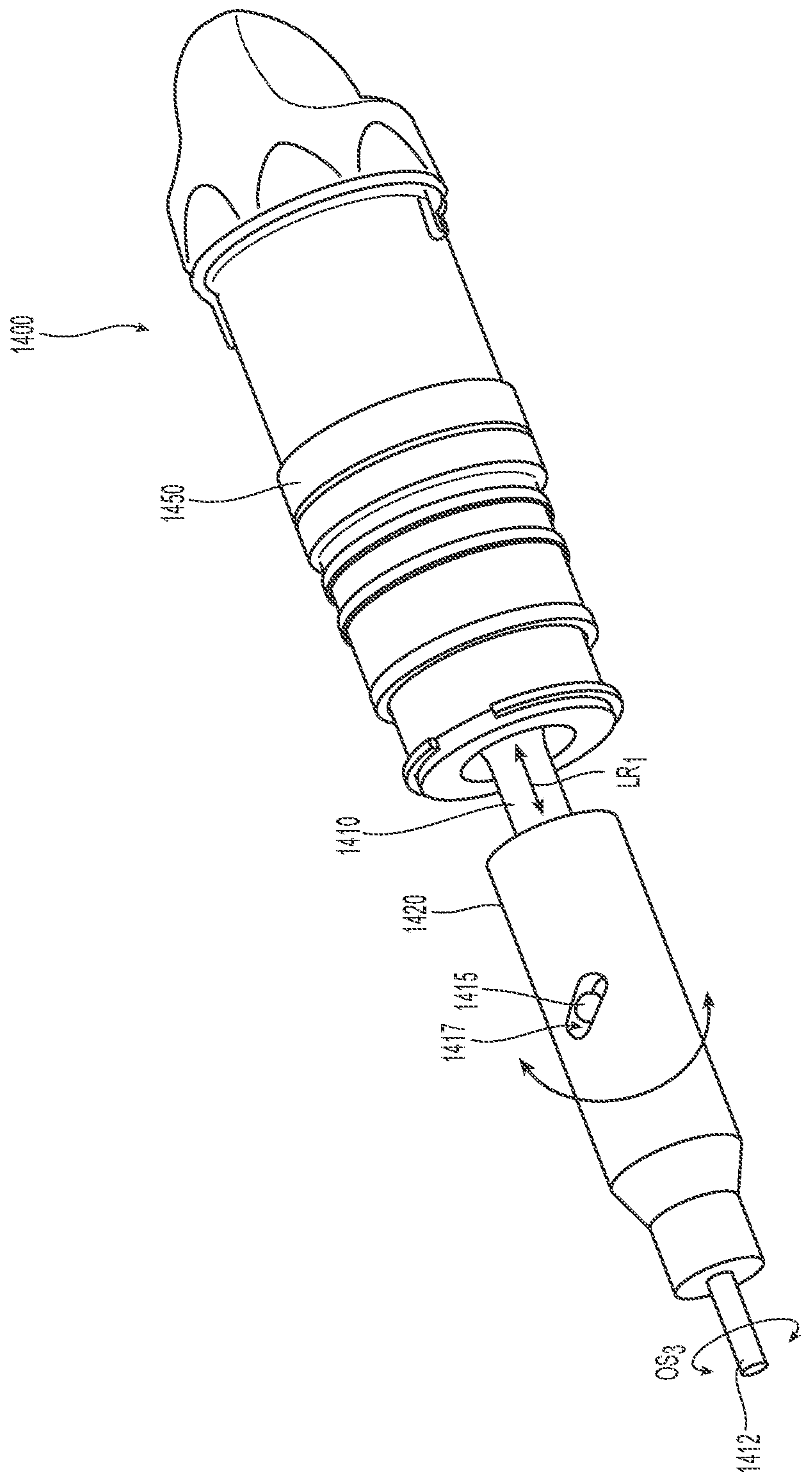
FIG. 24 is a schematic illustration of another alternate oscillation mechanism for use with the shaving surgical device including a mechanism that converts reciprocating motion to oscillatory output for controlling the shaft.

Turning to FIG. 24 which shows yet another embodiment of an oscillation mechanism 1400 in accordance with the present disclosure. Oscillation mechanism 1400 includes a housing 1420 that is configured to support multiple shafts and gear assemblies arranged in parallel fashion that extend from the proximal motor input to the gear assembly output to the oscillating surgical tool 100 similar to the surgical instruments described above. In this instance, the motor

1450 is configured to output reciprocating motion LR to shaft 1410 similar to a reciprocating saw or similar to some known ultrasonic surgical platforms. The reciprocating motion of the shaft 1410 is converted into oscillatory motion (See arrow OS3) of the tool shaft 1412 utilizing a helical groove 1417 and pin 1415 arrangement disposed within the housing 1420.

More particularly, the distal end of the shaft 1410 is operably coupled to the pin 1415 such that the pin 1415 reciprocates in unison therewith. Pin 1415, in turn, is configured to ride within helical groove 1417 which is operably associated with shaft 1412 such that, longitudinal reciprocation of pin 1415 within groove 1417 oscillates shaft 1412 as indicated by arrow OS3. Oscillation of shaft 1412 is translated to surgical tool 100 for a particular surgical purpose.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended hereto.

What is claimed is:

1. A surgical device for cutting or shaving bone or hard tissue, comprising:

an outer housing having a collet secured to an inner peripheral surface thereof including a series of apertures defined about a circumference therein;

a housing including an elongated tube extending from the housing, the elongated tube configured to support a surgical tool at a distal end thereof;

a gear assembly disposed within the housing and configured to drive the surgical tool, the gear assembly including a drive gear housing selectively moveable within the housing to switch the gear assembly between an oscillation mode and a rotation mode for driving the surgical tool; and a motor operably coupled to the gear assembly, such that, upon activation thereof, the motor at least one of oscillates or rotates the surgical tool depending upon the position of the drive gear housing within the housing.

2. The surgical device for cutting or shaving hard tissue according to claim 1, wherein the housing includes a slot defined in a proximal end thereof that communicates with a post that extends from the drive gear housing such that upon movement of the housing the slot correspondingly moves the post within the slot.

3. The surgical device for cutting or shaving hard tissue according to claim 2, wherein the slot is arcuate and the post moves within the slot upon rotation of the housing relative to the collet.

4. The surgical device for cutting or shaving hard tissue according to claim 3, further comprising a lever lock that operably couples to the housing and wherein, upon actuation, the lever lock allows a user to selective rotate the housing relative to the collet and, upon release, the lever lock allows a user to lock the lever lock in one of the series of apertures defined within the collet.

5. The surgical device for cutting or shaving hard tissue according to claim 1, wherein when disposed in the oscillation mode the gear assembly operably engages a link that oscillates a swing gear at a rotation angle β, the rotation angle β being dependent on the distance between an axis of the motor and an axis of the swing gear.

6. The surgical device for cutting or shaving hard tissue according to claim 5, wherein the distance between the axis of the motor and the axis of the swing gear changes upon rotation of the housing relative to the collet thereby changing the rotation angle β.

7. The surgical device for cutting or shaving hard tissue according to claim 5, further comprising a lever lock that operably couples to the housing and wherein, upon actuation, the lever lock allows a user to selective rotate the housing relative to the collet and, upon release, the lever lock allows a user to lock the lever lock in one of the series of apertures defined within the collet and wherein each of the series of apertures sets the rotation angle β of the swing gear.

8. The surgical device for cutting or shaving hard tissue according to claim 7, wherein at least one of the series of apertures defines a rotation angle β of the swing gear in the range of about 48° to about 64°, in the range of about 65° to about 72°, or in the range of about 73° to about 85°.

9. A surgical device for cutting or shaving bone or hard tissue, comprising:

an outer housing having a collet secured to an inner peripheral surface thereof including a series of apertures defined about a circumference therein;

a housing including an elongated tube extending from the housing, the elongated tube configured to support a surgical tool at a distal end thereof;

a gear assembly disposed within the housing and configured to drive the surgical tool, the gear assembly including a drive gear housing selectively moveable within the housing to switch the gear assembly between an oscillation mode and a rotation mode for driving the surgical tool; and a motor operably coupled to the gear assembly, such that, upon activation thereof, the motor at least one of oscillates or rotates the surgical tool depending upon the position of the drive gear housing within the housing, wherein when disposed in the rotational mode the gear assembly operably engages a direct drive gear that couples to an idle gear that drives the surgical tool.

10. The surgical device for cutting or shaving hard tissue according to claim 9, wherein the housing includes a slot defined in a proximal end thereof that communicates with a post that extends from the drive gear housing such that upon movement of the housing the slot correspondingly moves the post within the slot.

11. The surgical device for cutting or shaving hard tissue according to claim 10, wherein the slot is arcuate and the post moves within the slot upon rotation of the housing relative to the collet.

12. The surgical device for cutting or shaving hard tissue according to claim 11, further comprising a lever lock that operably couples to the housing and wherein, upon actuation, the lever lock allows a user to selective rotate the housing relative to the collet and, upon release, the lever lock allows a user to lock the lever lock in one of the series of apertures defined within the collet.

13. The surgical device for cutting or shaving hard tissue according to claim 12, wherein, upon actuation, the lever lock allows a user to selective rotate the housing relative to the collet and, upon release, the lever lock allows a user to lock the lever lock in one of the series of apertures defined within the collet and wherein rotation of the housing to one of the series of apertures, in turn, moves the drive gear housing to configure the surgical device in a rotational mode.

14. The surgical device for cutting or shaving hard tissue according to claim 13, wherein upon rotation of the housing relative to the collet, the post moves along the slot to disengage a series of gears associated with the oscillation mode and engage a series of gears associated with the rotational mode.

15. The surgical device for cutting or shaving hard tissue according to claim 14, wherein the drive gear housing includes a pin groove defined therein which is configured to at least partially seat the idle gear therein, the pin groove configured to restrict movement of the drive gear housing in a linear direction as the housing rotates.

16. A surgical device for cutting or shaving bone or hard tissue, comprising:

an outer housing having a collet secured to an inner peripheral surface thereof including a series of apertures defined about a circumference therein;

a housing including an elongated tube extending from the housing, the elongated tube configured to support a surgical tool at a distal end thereof;

a gear assembly disposed within the housing and configured to drive the surgical tool, the gear assembly including a drive gear housing selectively moveable within the housing to switch the gear assembly between an oscillation mode and a rotation mode for driving the surgical tool; and a motor operably coupled to the gear assembly, such that, upon activation thereof, the motor at least one of oscillates or rotates the surgical tool depending upon the position of the drive gear housing within the housing, wherein when disposed in the rotational mode the gear assembly operably engages a direct drive gear that couples to an idle gear that drives the surgical tool, wherein when disposed in the oscillation mode the gear assembly operably engages a link that oscillates a swing gear at a rotation angle β, the rotation angle β being dependent on the distance between the axis of the motor and the axis of the swing gear.

17. The surgical device for cutting or shaving hard tissue according to claim 16, wherein the housing includes a slot defined in a proximal end thereof that communicates with a post that extends from the drive housing such that upon movement of the housing the slot correspondingly moves the post within the slot.

18. The surgical device for cutting or shaving hard tissue according to claim 17, wherein the slot is arcuate and the post moves within the slot upon rotation of the housing relative to the collet.

19. The surgical device for cutting or shaving hard tissue according to claim 18, further comprising a lever lock that operably couples to the housing and wherein, upon actuation, the lever lock allows a user to selective rotate the housing relative to the collet and, upon release, the lever lock allows a user to lock the lever lock in one of the series of apertures defined within the collet.

20. The surgical device for cutting or shaving hard tissue according to claim 16, wherein the surgical tool includes a drill bit that is configured to cut or shave tissue when disposed in an oscillating mode or a rotation mode.

* * * * *